US007838041B2

(12) United States Patent
Raison et al.

(10) Patent No.: US 7,838,041 B2
(45) Date of Patent: Nov. 23, 2010

(54) METHOD FOR TREATING MULTIPLE MYELOMA

(75) Inventors: Robert Lindsay Raison, New South Wales (AU); Rosanne Dorothy Dunn, Manly (AU); Boon Hwa Andre Choo, Singapore (SG)

(73) Assignee: Immune System Therapeutics Ltd, Ultimo (AU)

( * ) Notice: Subject to any disclaimer, the term of this patent is extended or adjusted under 35 U.S.C. 154(b) by 274 days.

(21) Appl. No.: 12/016,462

(22) Filed: Jan. 18, 2008

(65) Prior Publication Data

US 2009/0263358 A1 Oct. 22, 2009

Related U.S. Application Data

(62) Division of application No. 10/481,212, filed as application No. PCT/AU02/00896 on Jul. 5, 2002, now Pat. No. 7,344,715.

(30) Foreign Application Priority Data

Jul. 6, 2001 (AU) .................................... PR6179

(51) Int. Cl.
*A61K 35/28* (2006.01)
*A61K 39/395* (2006.01)
(52) U.S. Cl. ...................................... 424/577; 424/800
(58) Field of Classification Search ....................... None
See application file for complete search history.

(56) References Cited

U.S. PATENT DOCUMENTS 6,632,927 B2 10/2003 Adair et al.

OTHER PUBLICATIONS

Axiak SM et al. "Quantitation of free κ light chains in serum and urine using a monoclonal antibody based inhibition enzyme-linked immunoassay", Journal of Immunological Methods (1987) vol. 99 (1) pp. 141-147.
Boux HA et al. "The surface expression of a tumor-associated antigen on human kappa myeloma cells", Eur. J. Immunol. (1984) 14:216-222.
Boux, H. et al. "A tumor associated antigen specific for kappa myeloma cell." J. Exp. Med., 158/5 pp. 1769-1774 (1983).
Dunn, R. et al. "Antigen binding and cytotoxic properties of a recombinant immunotoxin incorporating the lytic peptide, melittin." Immunotechnology, 2/3 pp. 229-240 (1996).
Izard, M. et al., "An improved method for labeling Monoclonal Antibodies with Samarium-153: Use of the Bifunctional Chelate 2-(p-Isothiocyanatobenzl)-6-methyldiethylenetriaminepentaacetic Acid." Bioconjugate Chem 3 /4 pp. 346-350 (1992).
Walker, K. et al., "A monoclonal antibody with selectivity for human kappa myeloma and lymphoma cells which has potential as a therapeutic agent." Adv. Exp Med. Biol., vol. 186 pp. 833-841 (1985).
Walker, K et al., "A rat model system for radioimmunodetection of kappa myeloma antigen on malignant B cells." Europ. J. Med 12/9 pp. 461-467 (1986).
Weston K. et al. "In vivo binding of mouse IgG via polyreactive surface IgM abrogates progressive lymphocytosis in prolymphocytic leukemia." Leukemia and Lymphoma, vol. 29, pp. 361-373 (1998).
Chauhan, D. and Anderson KC. "Apoptosis in Multiple Myeloma: Therapeutic Implications", (2001) Apoptosis. 6 (1-2): 47-55.
Drach, J. et al. "The Biology of Multiple Myeloma", (2000) Cancer Res Clin Oncol. 126:441-447.
Drayson, M. "Serum Free Light-Chain Measurements for Identifying and Monitoring Patients with Nonsecretory Multiple Myeloma" (2001) Blood 97 (9):2900-2902.
Goodnow et al. "Structural Analysis of the Myeloma-Associated Membrane Antigen KMA",(1985) J. Immunol. 135:1276-1280.
Kyle, RA. et al. "Update on the Treatment of Multiple Myeloma" (2001) The Oncologist. 6 (2):119-124.
Kyle, RA. "Clinical Aspects of Multiple Myeloma and Related Disorders Including Amyloidosis", (1999) Path Biol. 47(2):148-157.
Ludwig, H. et al. "Multiple Myeloma: An Update on Biology and Treatment", (1999) Annals Oncol. 10 (6):S31.
Feldman et al. Anti-TNF alpha therapy is useful in rheumatoid arthritis and Crohn's disease: analysis of the mechanism of action predicts utility in other diseases. Transplant. Proc. 1998, 30, 4126-4127.
Cochlovius et al. Modern Drug Discovery, 2003, pp. 33-38.
Paul, Fundamental Immunology, (textbook), 1999, under the heading Immunoglobulins: structure and Function, pp. 37, 43, 58, 59.
Rudikoff et al., Single amino acid substitution altering antigen-binding specificity. Proc Natl Acad Sci USA 1982, vol. 79, pp. 1979.
Ozaki et al. Humanized anti-HM1.24 antibody mediates myeloma cell cytotoxicity that is enhanced by cytokine stimulation of effector cells. Blood, 1999, vol. 11, pp. 3922-3930.
Siami et al. Plasmapheresis and paraproteinemia: cryoprotein-induced diseases, monoclonal gammopathy, Waldenström's macroglobulinemia, hyperviscosity syndrome, multiple myeloma, light chain disease, and amyloidosis. Therapeutic Aphreresis, Feb. 1999;3(1):8-19.
Blume, et al., A review of autologous hematopoietic cell transplantation., American Society for Blood and Marrow Transplantation, vol. 6, Issue 1, pp. 1-12 (Jan. 2000).

*Primary Examiner*—Michail A Belyavskyi
(74) *Attorney, Agent, or Firm*—Carol L. Francis; Bozicevic, Field & Francis, LLP

(57) ABSTRACT

The present invention relates to methods for the treatment of multiple myeloma. More particularly, the present invention relates to a method for inducing apoptosis in myeloma cells by administration of a K121-like antibody.

11 Claims, 25 Drawing Sheets

K121 Variable Genes

VH

| | | | | | | | | | | | | | | |
|---|---|---|---|---|---|---|---|---|---|---|---|---|---|---|
| Gln | Val | Gln | Leu | Gln | Gln | Ser | Gly | Ala | Glu | Leu | Val | Lys | Pro | Gly Ala | 16 |
| CAG | GTG | CAG | CTG | CAG | CAG | TCA | GGG | GCG | GAG | CTT | GTG | AAG | CCA | GGG GCC | 48 |

```
Gln Val Gln Leu Gln Gln Ser Gly Ala Glu Leu Val Lys Pro Gly Ala      16
CAG GTG CAG CTG CAG CAG TCA GGG GCG GAG CTT GTG AAG CCA GGG GCC      48

Ser Val Lys Leu Ser Cys Thr Ala Ser Gly Phe Asn Ile Lys Asp Thr      32
TCA GTC AAG TTG TCC TGT ACA GCT TCT GGC TTC AAC ATT AAA GAC ACC      96

Tyr Met His Trp Val Lys Gln Arg Pro Glu Gln Gly Leu Glu Trp Ile      48
TAT ATG CAC TGG GTG AAG CAG AGG CCT GAA CAG GGC CTG GAG TGG ATT     144

Gly Arg Ile Asp Pro Ala Asn Gly Asn Thr Lys Tyr Asp Pro Lys Phe      64
GGA AGG ATT GAT CCT GCG AAT GGT AAC ACT AAA TAT GAC CCG AAG TTC     192

Gln Gly Lys Ala Ala Ile Ile Ala Asp Thr Ser Ser Asn Thr Ala Tyr      80
CAG GGC AAG GCC GCT ATA ATA GCA GAC ACA TCC TCC AAC ACA GCC TAC     240

Leu Gln Leu Ser Ser Leu Thr Ser Glu Asp Thr Ala Val Tyr Tyr Cys      96
CTG CAG CTC AGC AGC CTG ACA TCT GAG GAC ACT GCC GTC TAT TAC TGT     288

Ala Arg Gly Val Tyr His Asp Tyr Asp Gly Asp Tyr Trp Gly Gln Gly     112
GCT AGG GGG GTC TAC CAT GAT TAC GAC GGG GAC TAC TGG GGC CAA GGG     336

Thr Thr Val Thr Val Ala Ser                                         119
ACC ACG GTC ACC GTC GCC TCC                                         357
```

VL

```
Asp Ile Val Met Thr Gln Ser Gln Lys Phe Met Ser Thr Ser Val Gly      16
GAC ATC GTC ATG ACC CAG TCT CAA AAA TTC ATG TCC ACA TCA GTA GGA      48

Asp Arg Val Ser Val Thr Cys Lys Ala Ser Gln Asn Val Gly Thr Asn      32
GAC AGG GTC AGC GTC ACC TGC AAG GCC AGT CAG AAT GTG GGT ACT AAT      96

Val Ala Trp Tyr Gln Gln Lys Pro Gly Gln Ser Pro Lys Ala Leu Ile      48
GTA GCC TGG TAT CAA CAG AAA CCA GGG CAA TCT CCT AAA GCA CTG ATT     144

Tyr Ser Thr Ser Tyr Arg Tyr Ser Gly Val Pro Asp Arg Phe Thr Gly      64
TAC TCG ACA TCC TAC CGG TAC AGT GGA GTC CCT GAT CGC TTC ACA GGC     192

Ser Gly Ser Gly Thr Asp Phe Thr Leu Thr Ile Ser Asn Val Gln Ser      80
AGT GGA TCT GGG ACA GAT TTC ACT CTC ACC ATC AGC AAT GTG CAG TCT     240

Glu Asp Leu Ala Glu Tyr Phe Cys Gln Gln Tyr Asn Ser Tyr Pro Tyr      96
GAA GAC TTG GCA GAG TAT TTC TGT CAG CAA TAT AAC AGC TAT CCG TAC     288

Thr Phe Gly Gly Gly Thr Lys Leu Glu Ile Lys                         107
ACG TTC GGA GGG GGG ACC AAG CTG GAA ATA AAG                         321
```

Figure 9(a)

K121 VH DNA SEQUENCE FOR OLIGONUCLEOTIDE EXTENSION (VHF) →

(VH1)
caggtgcagctgcagcagtcaggggcggagcttgtgaagccaggggcctcagtcaagttgtcctgtac
                                                                    caacaggacatgtcgaaga
                                                                                (VH2)

(VH3)
                                      tgaagcagaggcctgaacagggcctggagtggattggaagg
ccgaagttgtaatttctgtggatatacgtgacccacttcgtctccgg attgatcctgcgaatggtaaacactaaatatg
                        tgtgatttatactgggcttcaaggtcccgttccggcgatattatcgtctgtgtagg
                        (VH4)

(VH5)
            cacagcctacctgcagctcagcagcctgacatctgaggacactgccgtctattactgtgctagggggggtc
aggttgtgtcggatgga                                                                     gatcccccag
                                                                                                        (VH6)

atggtactaatgctgcccctgatgacccggttccctggtgccagtgg

← (VHR)

Figure 9(b)

K121 VL DNA SEQUENCE FOR OLIGONUCLEOTIDE EXTENSION (VLF)

(VL1)
gacatcgtcatgacccagtctcaaaaattcatgtccacatcagtaggagacagggtcagcgtcac
                                                cccagtcgcagtggacgttccgg
                                                         (VL2)

(VL3)
                                tcaacagaaaccagggcaatctcctaaagcactgatttactcg
tcagtcttacacccatgattacatcggaccatagttgtctttgg (VL5)
acatcctaccggtacagtggag                                      actctcaccatc
        gccatgtcacctcagggactagcgaagtgtccgtcacctagaccctgtctaaagtgagagtggtag
        (VL4)

agcaatgtgcagtctgaagacttggcagagtatttctgtcagcaatataac
                                cgttatattggtcgataggcatgtgcaagcctccc
                                                (VL6)

ccctggttcgacctttatttc
                    (VLR)

Figure 9(c)

PCR PRIMERS FOR OLIGONUCLEOTIDE EXTENSION OF K121 VH (VH1)
5' caggtgcagctgcagcagtcaggggcggagcttgtgaagccaggggcctcagtcaagttgtcctgtac 3'

(VH2)
5' ggcctctgcttcacccagtgcatataggtgtctttaatgttgaagccagaagctgtacaggacaac 3'

(VH3)
5' tgaagcagaggcctgaacagggcctggagtggattggaaggattgatcctgcgaatggtaacactaaatatg 3'

(VH4)
5'
aggtaggctgtgttggaggatgtgtctgctattatagcggccttgccctggaacttcgggtcatatttagtgt 3'

(VH5)
5' cacagcctacctgcagctcagcagcctgacatctgaggacactgccgtctattactgtgctaggggggtc 3'

(VH6)
5' ggtgaccgtggtcccttggccccagtagtccccgtcgtaatcatggtagacccccta 3'

(VHF)
5' caggtgcagctgcagcag 3'

(VHR)
5' ggtgaccgtggtcccttgg 3'

Figure 9(d)

PCR PRIMERS FOR OLIGONUCLEOTIDE EXTENSION OF K121 VL (VL1)
5' gacatcgtcatgacccagtctcaaaaattcatgtccacatcagtaggagacagggtcagcgtcac 3'

(VL2)
5' ggtttctgttgataccaggctacattagtacccacattctgactggccttgcaggtgacgctgaccc 3'

(VL3)
5' tcaacagaaaccagggcaatctcctaaagcactgatttactcgacatcctaccggtacagtggag 3'

(VL4)
5' gatggtgagagtgaaatctgtcccagatccactgcctgtgaagcgatcagggactccactgtaccg 3'

(VL5)
5' actctcaccatcagcaatgtgcagtctgaagacttggcagagtatttctgtcagcaatataac 3'

(VL6)
5' ctttatttccagcttggtccccctccgaacgtgtacggatagctgttatattgc 3'

(VLF)
5' gacatcgtcatgacccag 3'

(VLR)
5' ctttatttccagcttgg

Figure 9(e)

*PCR Primers*
VH
cK-VH-F     5'-GGG<u>GTGCAC</u>TCCCAGGTGCAGCTGCAGCAGTCA-3'
            Apa L1 cK-VH-R     5'-CGC<u>GGATCC</u>ACTCACCGGAGGCGACGGTGACCGTGG-3'
            Bam H1

VL
cK-VL-F     5'-GGG<u>GTGCAC</u>TCCGACATCGTCATGACCCAGTCT-3'
            Apa L1 cK-VL-R     5'-CGC<u>GGATCC</u>ACTCACCCTTTCTTTCCAGCTTGGTCC-3'
            Bam H1

TCC   recreates the last serine residue of the leader sequence.

ACTCACC is a splice acceptor site

Figure 10

Humanisation of K121 VL using a human VL gene as the framework.

THE DNA SEQUENCE OF A HUMAN FRAMEWORK VL AND K121 VL

```
                A
      ━━━━━━━━━▶
K121VL   GACATCGTCATGACCCAGTCTCAAAAATTCATGTCCACATCAGTAGGAGACAGGGTCAGC
hVL      GACATCCAAATGACCCAGTCTCCTTCCACCCTGTCTGCATCTGTAGGAGACAGAGTCACC
         ******  *************  *  ****  ****  *************  **** *
                                                            ◀━━━━━━
                              B
         ───────────────────────────────────────────▶
K121VL   GTCACCTGCAAGGCCAGTCAGAATGTGGGTACTAATGTAGCCTGGTATCAACAGAAACCA
hVL      ATCACTTGCCGGGCCAGTCAGGGTATTGGTAATTGGTTGGCCTGGTATCAGCAGAAACCA
         **** *** ********* *  * ****  *    ********** ********
         ◀━━━━━━━━━━
              E
                                       C
                 ────────────────────────────────────────▶
K121VL   GGGCAATCTCCTAAAGCACTGATTTACTCGACATCCTACCGGTACAGTGGAGTCCCTGAT
hVL      GGGACAGCCCCTAAACTCCTGATCTCTAAGGCGTCTAGTTTACAAAGTGGGGTCCCATCA
         ***  *  * ******  **** *  *   * *  ** ** *     *****  ***
                    ◀──────────
                        F

K121VL   CGCTTCACAGGCAGTGGATCTGGGACAGATTTCACTCTCACCATCAGCAATGTGCAGTCT
hVL      AGGATCAGCGGCAGTGGATTTGGGACAGAATTCACTCTCACCATCAGCAGCCTGCAGCCT
         *  ***  ********* * ******** **************************  **

D
         ────────────────────────────────────────────▶
K121VL   GAAGACTTGGCAGAGTATTTCTGTCAGCAATATAACAGCTATCCGTACACGTTCGGAGGG
hVL      GATGATTTTGCAACTTATTACTGCCAACCCTATAATGATTAT---TTCAGTTTCGGTGGA
         ** ** ** ***   ****  ***  **   ***** *  ***   * **  ***** **
                   ◀──────────
                       G

K121VL   GGGACCAAGCTGGAAATAAAG---
hVL      GGGACCAGGGTGGAGATGAAACGA
         *******  * **** ** **
                          ◀━━━━━━━━━
                              H
```

Figure 14(b)

OLIGONUCLEOTIDES FOR K121 VL HUMANISATION USING PCR

VLA
5' ggggtgcactccgacatccaaatgacccag 3'
    Apa L1

VLB
5' atcacttgcaaggccagtcagaatgtgggtactaatgtagcctggtatcag 3'

VLC
5' ctcctgatctactcgacatcctaccggtacagtggggtccca 3'
                          Age 1

VLD
5' acttattactgccagcaatataacagctatccgtacacgttcggtgga 3'

VLE
5' gcaagtgatggtgactctg 3'

VLF
5' gtagatcaggagtttagg 3'

VLG
5' gcagtaataagttgcaaa 3'

VLH
5' gccggatccactcacctttcatctccaccct 3'
    BamH1

Figure 14(c)

DNA SEQUENCE OF K121 AND HUMAN VH3 (hVH) VARIABLE HEAVY CHAIN GENES

```
K121VH    CAGGTGCAGCTGCAGCAGTCAGGGGCGGAGCTTGTGAAGCCAGGGGCCTCAGTCAAGTTG
hVH       CAGGTGCAGCTGCTGGAGTCTGGGGGAGGCGTGGTCCAGCCTGGGAGGTCCCTGAGACTC
          ************* * **** ****  *   * **  **** ***  **  * *    *

K121VH    TCCTGTACAGCTTCTGGCTTCAACATTAAAGACACCTATATGCACTGGGTGAAGCAGAGG
hVH       TCTTGTGTAGCGTCTGGATTCACCTTCAGTATCTATGACATGCACTGGGTCCGCCAGGCT
          ** *** *** ***** **** *  *       *  * * ********** *   ***

K121VH    CCTGAACAGGGCCTGGAGTGGATTGGAAGGATTGATCCTGCGAATGGTAACACTAAATA
hVH       CCAGGCAAGGGGCTGGAGTGGGTGGCACTTATGCTATATGATGGAAGTCTTAAATATTA
          ** *  **** ********* *  *   *  **     **    **    * **

K121VH    TGACCCGAAGTTCCAGGGCAAGGCCGCTATAATAGCAGACACATCCTCCAACACAGC
hVH       TGGAGACTCCGTGAAGGGCCGATTCACCATCTCCAGAGACAATTCCAAGAACACACT
          **         *  *****      *  * **     *****   ***  ******

K121VH    CTACCTGCAGCTCAGCAGCCTGACATCTGAGGACACTGCCGTCTATTACTGTGCTAGGGG
hVH       CTATCTGCAAATGAACAGCCTGAGAGCCGACGACACGGCTGTGTATTACTGTGCGAGAGG
          *** *****    * * *******  *  *  *****  **  ********** ** **

K121VH    GGTCTACCATGATTACGACGGGGACTACTGGGGCCAAGGGACCACGGTCACCAT
hVH       CCGATCTCGTCTGCTTATCACGCCCTCTTGGGGCCGGGGAACCCTGGTCACCGT
             *  *      *   *  **  ******  **  ****   *** *

K121VH    CGCCTCC
hVH       CTCCTCA
          * ****
```

Figure 15(a)

Humanisation of K121 VH mutagenesis primers

VHAf

CACCTTCAGTGACACCTATATGCACTGGGTCAAGCAGGCTCCAGG

VHAr

CCTGGAGCCTGCTTGACCCAGTGCATATAGGTGTGACTGAAGGTG

VHB1f

GTGGGTGGCAAGGATT*GATCCTGCG*GGAAGTCTT

VHB1r

AAGACTTCCCGCAGGATCAATCCTTGCCACCCAC

VHB2f

*TGATCCTGCG*AATGGTAACC*ACTAAATATG*GAGACT

VHB2r

AGTCTCCATATTTAGTGGTTACCATTCGCAGGATCA

VHB3f

*ACTAAATATG*ACCCGAAGTTCCAGGGCCGATTC

VHB3r

GAATCGGCCCTGGAACTTCGGGTCATATTTAGT

VHCf

TGCGAGAGGGGTCTACCATGATTACGACGGGGACTACTGGGGCC
G

VHCr

CGGCCCCAGTAGTCCCCGTCGTAATCATGGTAGACCCCTCTCGCA

Figure 15(b)

SEQUENCE LISTING

```
<160> NUMBER OF SEQ ID NOS: 50

<210> SEQ ID NO 1
<211> LENGTH: 119
<212> TYPE: PRT
<213> ORGANISM: Mus musculus

<400> SEQUENCE: 1

Gln Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45
```

Gly Arg Ile Asp Pro Ala Asn Gly Asn Thr Lys Tyr Asp Pro Lys Phe
    50                  55                  60

Gln Gly Lys Ala Ala Ile Ile Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Gly Val Tyr His Asp Tyr Asp Gly Asp Tyr Trp Gly Gln Gly
            100                 105                 110

Thr Thr Val Thr Val Ala Ser
        115

<210> SEQ ID NO 2
<211> LENGTH: 357
<212> TYPE: DNA
<213> ORGANISM: Mus musculus

<400> SEQUENCE: 2
caggtgcagc tgcagcagtc aggggcggag cttgtgaagc caggggcctc agtcaagttg      60
tcctgtacag cttctggctt caacattaaa gacacctata tgcactgggt gaagcagagg     120
cctgaacagg gcctggagtg gattggaagg attgatcctg cgaatggtaa cactaaatat     180
gacccgaagt tccagggcaa ggccgctata tagcagaca catcctccaa cacagcctac     240
ctgcagctca gcagcctgac atctgaggac actgccgtct attactgtgc tagggggtc      300 taccatgatt acgacgggga ctactggggc caagggacca cggtcaccgt cgcctcc        357

<210> SEQ ID NO 3
<211> LENGTH: 107
<212> TYPE: PRT
<213> ORGANISM: Mus musculus

<400> SEQUENCE: 3

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Thr Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Gly Gly Thr Lys Leu Glu Ile Lys
            100                 105

<210> SEQ ID NO 4
<211> LENGTH: 321
<212> TYPE: DNA
<213> ORGANISM: Mus musculus

<400> SEQUENCE: 4
gacatcgtca tgacccagtc tcaaaaattc atgtccacat cagtaggaga cagggtcagc      60
gtcacctgca aggccagtca gaatgtgggt actaatgtag cctggtatca acagaaacca     120
gggcaatctc ctaaagcact gatttactcg acatcctacc ggtacagtgg agtccctgat     180
cgcttcacag gcagtggatc tgggacagat ttcactctca ccatcagcaa tgtgcagtct     240
gaagacttgg cagagtattt ctgtcagcaa tataacagct atccgtacac gttcggaggg    300
gggaccaagc tggaaataaa g    321

<210> SEQ ID NO 5
<211> LENGTH: 68
<212> TYPE: DNA
<213> ORGANISM: Mus musculus

<400> SEQUENCE: 5
caggtgcagc tgcagcagtc aggggcggag cttgtgaagc caggggcctc agtcaagttg    60
tcctgtac    68

<210> SEQ ID NO 6
<211> LENGTH: 66
<212> TYPE: DNA
<213> ORGANISM: Mus musculus

<400> SEQUENCE: 6
caacaggaca tgtcgaagac cgaagttgta atttctgtgg atatacgtga cccacttcgt    60
ctccgg    66

<210> SEQ ID NO 7
<211> LENGTH: 73
<212> TYPE: DNA
<213> ORGANISM: Mus musculus

<400> SEQUENCE: 7
tgaagcagag gcctgaacag ggcctggagt ggattggaag gattgatcct gcgaatggta    60
aacactaaat atg    73

<210> SEQ ID NO 8
<211> LENGTH: 73
<212> TYPE: DNA
<213> ORGANISM: Mus musculus

<400> SEQUENCE: 8
tgtgatttat actgggcttc aaggtcccgt tccggcgata ttatcgtctg tgtaggaggt    60
tgtgtcggat gga    73

<210> SEQ ID NO 9
<211> LENGTH: 70
<212> TYPE: DNA
<213> ORGANISM: Mus musculus

<400> SEQUENCE: 9
cacagcctac ctgcagctca gcagcctgac atctgaggac actgccgtct attactgtgc    60
tagggggtc    70

<210> SEQ ID NO 10
<211> LENGTH: 59
<212> TYPE: DNA
<213> ORGANISM: Mus musculus

<400> SEQUENCE: 10 gatccccca gatggtacta atgctgcccc tgatgacccc ggttccctgg tgccagtgg    59

<210> SEQ ID NO 11
<211> LENGTH: 65
<212> TYPE: DNA

<213> ORGANISM: Mus musculus

<400> SEQUENCE: 11

```
gacatcgtca tgacccagtc tcaaaaattc atgtccacat cagtaggaga cagggtcagc    60
gtcac                                                                65
```

<210> SEQ ID NO 12
<211> LENGTH: 67
<212> TYPE: DNA
<213> ORGANISM: Mus musculus

<400> SEQUENCE: 12

```
cccagtcgca gtggacgttc cggtcagtct tacacccatg attacatcgg accatagttg    60
tctttgg                                                              67
```

<210> SEQ ID NO 13
<211> LENGTH: 65
<212> TYPE: DNA
<213> ORGANISM: Mus musculus

<400> SEQUENCE: 13

```
tcaacagaaa ccagggcaat ctcctaaagc actgatttac tcgacatcct accggtacag    60
tggag                                                                65
```

<210> SEQ ID NO 14
<211> LENGTH: 66
<212> TYPE: DNA
<213> ORGANISM: Mus musculus

<400> SEQUENCE: 14

```
gccatgtcac ctcagggact agcgaagtgt ccgtcaccta gaccctgtct aaagtgagag    60
tggtag                                                               66
```

<210> SEQ ID NO 15
<211> LENGTH: 63
<212> TYPE: DNA
<213> ORGANISM: Mus musculus

<400> SEQUENCE: 15

```
actctcacca tcagcaatgt gcagtctgaa gacttggcag agtatttctg tcagcaatat    60
aac                                                                  63
```

<210> SEQ ID NO 16
<211> LENGTH: 56
<212> TYPE: DNA
<213> ORGANISM: Mus musculus

<400> SEQUENCE: 16

```
cgttatattg gtcgataggc atgtgcaagc ctcccccctg gttcgacctt tatttc        56
```

<210> SEQ ID NO 17
<211> LENGTH: 66
<212> TYPE: DNA
<213> ORGANISM: Mus musculus

<400> SEQUENCE: 17

```
ggcctctgct tcacccagtg catataggtg tctttaatgt tgaagccaga agctgtacag    60
gacaac                                                               66
```

<210> SEQ ID NO 18
<211> LENGTH: 73
<212> TYPE: DNA
<213> ORGANISM: Mus musculus

<400> SEQUENCE: 18
aggtaggctg tgttggagga tgtgtctgct attatagcgg ccttgccctg gaacttcggg    60
tcatatttag tgt                                                      73

<210> SEQ ID NO 19
<211> LENGTH: 58
<212> TYPE: DNA
<213> ORGANISM: Mus musculus

<400> SEQUENCE: 19
ggtgaccgtg gtcccttggc cccagtagtc cccgtcgtaa tcatggtaga cccccta      58

<210> SEQ ID NO 20
<211> LENGTH: 18
<212> TYPE: DNA
<213> ORGANISM: Mus musculus

<400> SEQUENCE: 20
caggtgcagc tgcagcag                                                 18

<210> SEQ ID NO 21
<211> LENGTH: 19
<212> TYPE: DNA
<213> ORGANISM: Mus musculus

<400> SEQUENCE: 21
ggtgaccgtg gtcccttgg                                                19

<210> SEQ ID NO 22
<211> LENGTH: 67
<212> TYPE: DNA
<213> ORGANISM: Mus musculus

<400> SEQUENCE: 22
ggtttctgtt gataccaggc tacattagta cccacattct gactggcctt gcaggtgacg    60
ctgaccc                                                             67

<210> SEQ ID NO 23
<211> LENGTH: 66
<212> TYPE: DNA
<213> ORGANISM: Mus musculus

<400> SEQUENCE: 23
gatggtgaga gtgaaatctg tcccagatcc actgcctgtg aagcgatcag ggactccact    60
gtaccg                                                              66

<210> SEQ ID NO 24
<211> LENGTH: 55
<212> TYPE: DNA
<213> ORGANISM: Mus musculus

<400> SEQUENCE: 24
ctttatttcc agcttggtcc cccctccgaa cgtgtacgga tagctgttat attgc        55

<210> SEQ ID NO 25
<211> LENGTH: 18
<212> TYPE: DNA

```
<213> ORGANISM: Mus musculus

<400> SEQUENCE: 25
gacatcgtca tgacccag                                                      18

<210> SEQ ID NO 26
<211> LENGTH: 17
<212> TYPE: DNA
<213> ORGANISM: Mus musculus

<400> SEQUENCE: 26
ctttatttcc agcttgg                                                       17

<210> SEQ ID NO 27
<211> LENGTH: 33
<212> TYPE: DNA
<213> ORGANISM: Artificial Sequence
<220> FEATURE:
<223> OTHER INFORMATION: PCR primer

<400> SEQUENCE: 27
ggggtgcact cccaggtgca gctgcagcag tca                                     33

<210> SEQ ID NO 28
<211> LENGTH: 36
<212> TYPE: DNA
<213> ORGANISM: Artificial Sequence
<220> FEATURE:
<223> OTHER INFORMATION: PCR Primer

<400> SEQUENCE: 28
cgcggatcca ctcaccggag gcgacggtga ccgtgg                                  36

<210> SEQ ID NO 29
<211> LENGTH: 33
<212> TYPE: DNA
<213> ORGANISM: Artificial Sequence
<220> FEATURE:
<223> OTHER INFORMATION: PCR Primer

<400> SEQUENCE: 29
ggggtgcact ccgacatcgt catgacccag tct                                     33

<210> SEQ ID NO 30
<211> LENGTH: 36
<212> TYPE: DNA
<213> ORGANISM: Artificial Sequence
<220> FEATURE:
<223> OTHER INFORMATION: PCR Primer

<400> SEQUENCE: 30
cgcggatcca ctcacccttt ctttccagct tggtcc                                  36

<210> SEQ ID NO 31
<211> LENGTH: 321
<212> TYPE: DNA
<213> ORGANISM: Homo sapiens

<400> SEQUENCE: 31
gacatccaaa tgacccagtc tccttccacc ctgtctgcat ctgtaggaga cagagtcacc        60
atcacttgcc gggccagtca gggtattggt aattggttgg cctggtatca gcagaaacca      120
gggacagccc ctaaactcct gatctctaag gcgtctagtt tacaaagtgg ggtcccatca      180
aggatcagcg gcagtggatt tgggacagaa ttcactctca ccatcagcag cctgcagcct      240
```
gatgattttg caacttatta ctgccaaccc tataatgatt atttcagttt cggtggaggg   300
accagggtgg agatgaaacg a   321

<210> SEQ ID NO 32
<211> LENGTH: 30
<212> TYPE: DNA
<213> ORGANISM: Artificial Sequence
<220> FEATURE:
<223> OTHER INFORMATION: PCR Primer

<400> SEQUENCE: 32
ggggtgcact ccgacatcca aatgacccag   30

<210> SEQ ID NO 33
<211> LENGTH: 51
<212> TYPE: DNA
<213> ORGANISM: Artificial Sequence
<220> FEATURE:
<223> OTHER INFORMATION: PCR Primer

<400> SEQUENCE: 33
atcacttgca aggccagtca gaatgtgggt actaatgtag cctggtatca g   51

<210> SEQ ID NO 34
<211> LENGTH: 42
<212> TYPE: DNA
<213> ORGANISM: Artificial Sequence
<220> FEATURE:
<223> OTHER INFORMATION: PCR Primer

<400> SEQUENCE: 34
ctcctgatct actcgacatc ctaccggtac agtggggtcc ca   42

<210> SEQ ID NO 35
<211> LENGTH: 48
<212> TYPE: DNA
<213> ORGANISM: Artificial Sequence
<220> FEATURE:
<223> OTHER INFORMATION: PCR Primer

<400> SEQUENCE: 35
acttattact gccagcaata taacagctat ccgtacacgt tcggtgga   48

<210> SEQ ID NO 36
<211> LENGTH: 19
<212> TYPE: DNA
<213> ORGANISM: Artificial Sequence
<220> FEATURE:
<223> OTHER INFORMATION: PCR Primer

<400> SEQUENCE: 36
gcaagtgatg gtgactctg   19

<210> SEQ ID NO 37
<211> LENGTH: 18
<212> TYPE: DNA
<213> ORGANISM: Artificial Sequence
<220> FEATURE:
<223> OTHER INFORMATION: PCR Primer

<400> SEQUENCE: 37
gtagatcagg agtttagg   18

<210> SEQ ID NO 38

```
<211> LENGTH: 18
<212> TYPE: DNA
<213> ORGANISM: Artificial Sequence
<220> FEATURE:
<223> OTHER INFORMATION: PCR Primer

<400> SEQUENCE: 38
gcagtaataa gttgcaaa                                                   18

<210> SEQ ID NO 39
<211> LENGTH: 31
<212> TYPE: DNA
<213> ORGANISM: Artificial Sequence
<220> FEATURE:
<223> OTHER INFORMATION: PCR Primer

<400> SEQUENCE: 39
gccggatcca ctcacctttc atctccaccc t                                    31

<210> SEQ ID NO 40
<211> LENGTH: 357
<212> TYPE: DNA
<213> ORGANISM: Homo sapiens

<400> SEQUENCE: 40
caggtgcagc tgctggagtc tgggggaggc gtggtccagc ctgggaggtc cctgagactc      60
tcttgtgtag cgtctggatt caccttcagt atctatgaca tgcactgggt ccgccaggct     120
ccaggcaagg ggctggagtg ggtggcactt atgctatatg atggaagtct taaatattat     180
ggagactccg tgaagggccg attcaccatc tccagagaca attccaagaa cacactctat     240
ctgcaaatga acagcctgag agccgacgac acggctgtgt attactgtgc gagaggccga     300
tctcgtctgc ttatcacgcc ctcttgggc cggggaaccc tggtcaccgt ctcctca         357

<210> SEQ ID NO 41
<211> LENGTH: 45
<212> TYPE: DNA
<213> ORGANISM: Artificial Sequence
<220> FEATURE:
<223> OTHER INFORMATION: PCR Primer

<400> SEQUENCE: 41
caccttcagt gacacctata tgcactgggt caagcaggct ccagg                     45

<210> SEQ ID NO 42
<211> LENGTH: 45
<212> TYPE: DNA
<213> ORGANISM: Artificial Sequence
<220> FEATURE:
<223> OTHER INFORMATION: PCR Primer

<400> SEQUENCE: 42
cctggagcct gcttgaccca gtgcatatag gtgtgactga aggtg                     45

<210> SEQ ID NO 43
<211> LENGTH: 34
<212> TYPE: DNA
<213> ORGANISM: Artificial Sequence
<220> FEATURE:
<223> OTHER INFORMATION: PCR Primer

<400> SEQUENCE: 43
gtgggtggca aggattgatc ctgcgggaag tctt                                 34
```

<210> SEQ ID NO 44
<211> LENGTH: 34
<212> TYPE: DNA
<213> ORGANISM: Artificial Sequence
<220> FEATURE:
<223> OTHER INFORMATION: PCR Primer

<400> SEQUENCE: 44
aagacttccc gcaggatcaa tccttgccac ccac         34

<210> SEQ ID NO 45
<211> LENGTH: 36
<212> TYPE: DNA
<213> ORGANISM: Artificial Sequence
<220> FEATURE:
<223> OTHER INFORMATION: PCR Primer

<400> SEQUENCE: 45
tgatcctgcg aatggtaacc actaaatatg gagact       36

<210> SEQ ID NO 46
<211> LENGTH: 36
<212> TYPE: DNA
<213> ORGANISM: Artificial Sequence
<220> FEATURE:
<223> OTHER INFORMATION: PCR Primer

<400> SEQUENCE: 46
agtctccata tttagtggtt accattcgca ggatca       36

<210> SEQ ID NO 47
<211> LENGTH: 33
<212> TYPE: DNA
<213> ORGANISM: Artificial Sequence
<220> FEATURE:
<223> OTHER INFORMATION: PCR Primer

<400> SEQUENCE: 47
actaaatatg acccgaagtt ccagggccga ttc          33

<210> SEQ ID NO 48
<211> LENGTH: 33
<212> TYPE: DNA
<213> ORGANISM: Artificial Sequence
<220> FEATURE:
<223> OTHER INFORMATION: PCR Primer

<400> SEQUENCE: 48
gaatcggccc tggaacttcg ggtcatattt agt          33

<210> SEQ ID NO 49
<211> LENGTH: 45
<212> TYPE: DNA
<213> ORGANISM: Artificial Sequence
<220> FEATURE:
<223> OTHER INFORMATION: PCR Primer

<400> SEQUENCE: 49
tgcgagaggg gtctaccatg attacgacgg ggactactgg ggccg    45

<210> SEQ ID NO 50
<211> LENGTH: 45
<212> TYPE: DNA
<213> ORGANISM: Artificial Sequence
<220> FEATURE:
<223> OTHER INFORMATION: PCR Primer -continued

```
<400> SEQUENCE: 50
cggccccagt agtcccgtc gtaatcatgg tagaccctc tcgca              45
```

METHOD FOR TREATING MULTIPLE MYELOMA

CROSS-REFERENCE TO RELATED APPLICATIONS

This application is a divisional of U.S. application Ser. No. 10/481,212, filed on Jun. 4, 2004, now issued as U.S. Pat. No. 7,344,715, which is the national stage application under 35 U.S.C. 371(c)(1) of PCT/AU02/00896 filed Jul. 5, 2002, which claims priority benefit of Australian application No. PR6179 filed Jul. 6, 2001.

FIELD OF THE INVENTION

The present invention relates to methods for the treatment of multiple myeloma. More particularly, the present invention relates to a method for inducing apoptosis in myeloma cells by administration of a K121-like antibody.

BACKGROUND OF THE INVENTION

Multiple myeloma (MM) is a B-cell malignancy characterised by the accumulation of terminally differentiated B-cells (plasma cells) in the bone marrow. Recent research has identified some of the genetic and molecular defects that occur in myelomatous plasma cells (Drach, J. et al. (2000) Cancer Res Clin Oncol. 126:441; Ludwig, H. et al. (1999) Annals Oncol. 10 (6):S31). These data indicate that multiple molecular events result in profound genetic instability of the cells, resistance to chemotherapy and increased bone marrow neovascularisation. The current therapy for MM is high dose chemotherapy and/or autologous peripheral blood stem cell transplantation. At present, the latter treatment is favoured due to a higher 5 year survival rate (52% versus 12%). Recently, antiangiogenic agents such as Thalidomide have produced an objective response in approximately 30% of refractory patients. MM is irreversibly fatal despite these drastic therapies, with median survival times of 4-6 years depending on mode of treatment (Kyle, R A. et al. (2001) The Oncologist. 6 (2):119).

There are currently 40,000 patients with MM in the United States, with an estimate that approximately 14,000 new patients are diagnosed each year (Chauhan, D. and Anderson K C. (2001) Apoptosis. 6 (1-2): 47). The incidence of MM worldwide is between 1.5-4.5/100,000/year depending on the country (Hurez, D. (1993) Revue du Praticien. 43(3):271).

The malignant B-cells in MM produce excess amounts of light chain, a component of immunoglobulin, and these light chains are present in the serum and urine of individuals with this disease. Approximately 70% of MM patients produce light chains of kappa-type, with the remaining 30% being lambda-type (Kyle, R A. (1999) Path Biol. 47(2):148).

K121 is a murine monoclonal antibody (mAb) that specifically recognises human free kappa light chains and an antigen expressed on the surface of kappa-type myeloma cells. This antigen is designated kappa myeloma antigen or KMA (Boux, H A. et al. (1983) J Exp Med. 158:1769). It has been established that KMA consists of free kappa light chains expressed in non-covalent association with actin on the cell membrane (Goodnow et al. (1985) J. Immunol. 135:1276). K121 does not exhibit cross-reactivity with any normal or malignant lymphoid cells or with intact human immunoglobulin molecules (Boux, H A et al. (1984) Eur. J. Immunol. 14: 216).

A quantitative immunoassay for measuring free kappa light chains in the serum and urine of patients suffering from MM has been developed using K121 (Axiak, S M. (1987) J Immunol Methods. 99:141). The recent literature suggests that quantification of free light chains may be used to monitor the progress and response to therapy of these patients (Drayson, M. (2001) Blood 97 (9):2900).

It has also been suggested that K121 may be used to deliver cytotoxins to kappa myeloma cells (Goodnow et al. (1985) J. Immunol. 135:1276). Indeed, an immunotoxin comprising the cytolytic peptide melittin linked to a K121 scFV fragment (scFv-mel) has been developed as a potential therapeutic agent for the treatment of MM (Dunn, R D. et al., (1996) Immunotechnology 2: 229).

SUMMARY OF THE INVENTION

The present inventors have now found that K121 alone (i.e. not conjugated to a toxin or a cytolytic agent) is capable of killing KMA bearing cells by induction of apoptosis. Furthermore, the present inventors have demonstrated that K121 alone can prevent the growth of tumour cells in vivo. These findings indicate that K121-like antibodies are potentially useful as primary therapeutic agents in the treatment of multiple myeloma.

Accordingly, in a first aspect the present invention provides a method for the treatment of kappa-type multiple myeloma in a subject, the method comprising administering to the subject an effective amount of a K121-like antibody, wherein the K121-like antibody is not conjugated to a toxin or a cytolytic agent.

The present invention also provides the use of a K121-like antibody for the preparation of a medicament for the treatment of kappa-type multiple myeloma, wherein the K121-like antibody is not conjugated to a toxin or a cytolytic agent.

In a preferred embodiment of the first aspect the method further comprises the step of treating the subject to reduce the levels of free kappa light chains present in the fluid of the subject prior to administration of the K121-like antibody. Preferably, the levels of free kappa light chains present in the serum of the subject are reduced. A reduction in the levels of free kappa light chains may be achieved by, for example, plasmapharesis. It is preferred that the treatment for reducing levels of free kappa light chains is performed on the subject just prior to administration of the K121-like antibody.

In a second aspect, the present invention provides a method for autologous hematopoietic cell transplantation in a subject, the method comprising (i) removing a hematopoietic progenitor cell population from the subject, (ii) treating the cell population with a K121-like antibody, and (iii) transplanting the treated cell population from step (ii) into the subject, wherein the K121-like antibody is not conjugated to a toxin or a cytolytic agent.

In a preferred embodiment of the second aspect, the method also involves intravenous infusion of a K121-like antibody into the subject.

In a preferred embodiment of the second aspect, the method of autologous transplantation is performed on the subject during or after cytoreductive therapy.

In a third aspect the present invention provides a method for killing kappa-type myeloma cells in a mixed population of cells, the method comprising contacting the mixed population of cells with a K121-like antibody, wherein the K121-like antibody is not conjugated to a toxin or a cytolytic agent.

In a fourth aspect the present invention provides a method for inducing apoptosis in KMA bearing cells, the method comprising exposing the cells to a K121-like antibody, wherein the K121-like antibody is not conjugated to a toxin or a cytolytic agent.

In a preferred embodiment of the fourth aspect, the KMA bearing cells are kappa-type myeloma cells.

In one embodiment of the present invention, the K121-like antibody comprises the CDR loops (CDR1, CDR2 and CDR 3) of the K121 antibody as shown in FIG. 9a. In another embodiment, the K121-like antibody comprises the VH and VL genes of the K121 antibody as shown in FIG. 9a.

In a further preferred embodiment of the present invention, the K121-like antibody is a chimaeric antibody or a humanised antibody.

BRIEF DESCRIPTION OF THE FIGURES

FIG. 10. PCR primers for PCR amplification of K121 VH and VL genes. The restriction enzyme sites for directional cloning into the mammalian expression vectors are underlined. The cK-VH-R and cK-VL-R primers include a splice acceptor site (shown in bold).

FIG. 15 (a) DNA sequence of K121 and human VH3 (hVH) variable heavy chain genes. (b) VH mutagenesis primers for use in humanisation of K121.

DETAILED DESCRIPTION OF THE INVENTION

Figure 1:
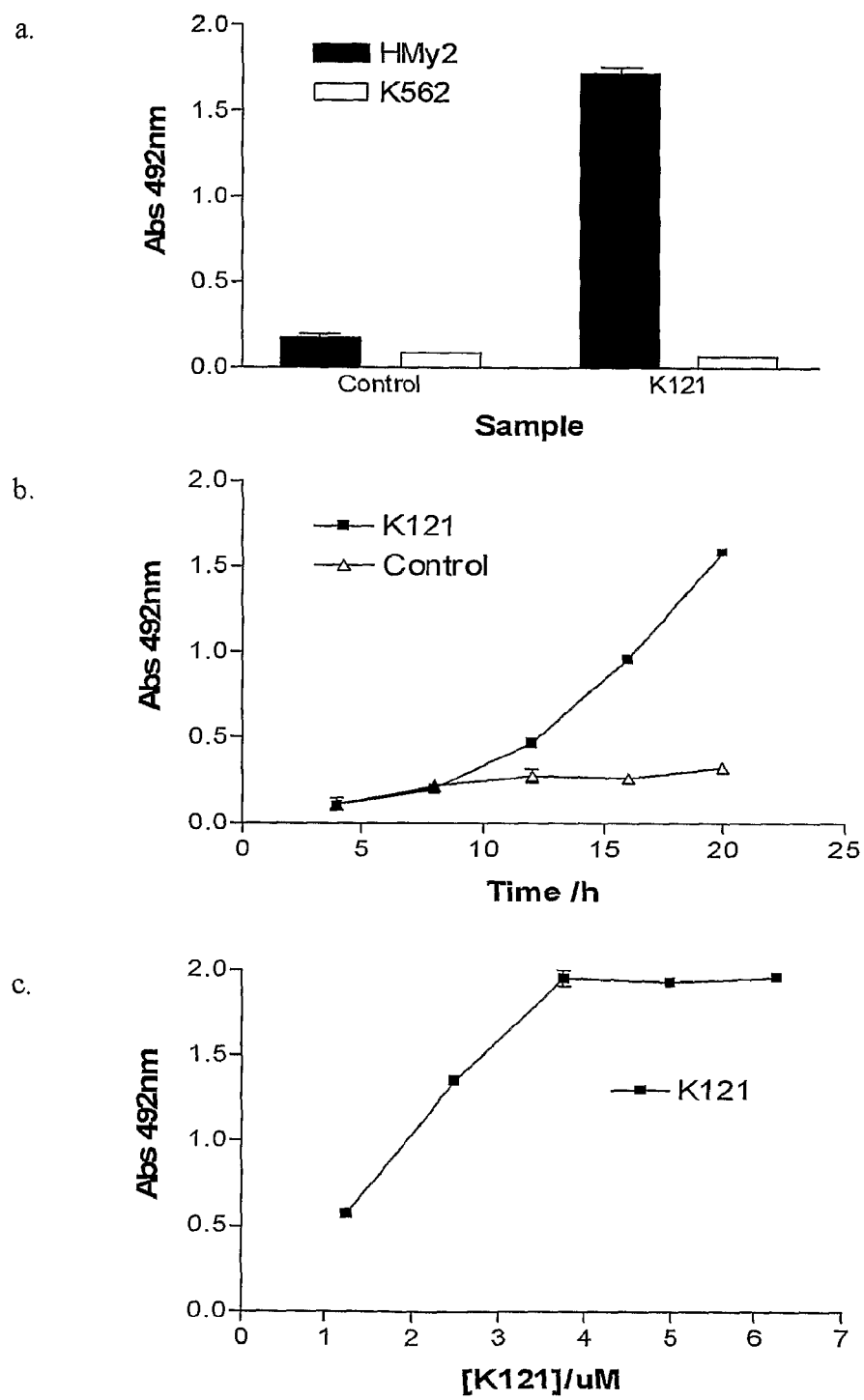
FIG. 1. (a) Cytotoxic activity of mAb K121 on HMy2 and K562 lymphoblastoid cells as measured by the leakage of cytoplasmic LDH (absorbance at 492 nm). Cells incubated for 20 h in the presence and absence of K121 mAb (6.25 uM) (b) Kinetics of K121 induced cell death (c) Concentration dependence of killing of HMy2 cells by K121.

When used herein, the phrase "K121-like antibody" refers to an antibody that competes with an antibody having the VH and VL regions shown in FIG. 9a for binding to kappa-type myeloma cells. Preferably, the term "K121-like antibody" refers to an antibody that binds to the same epitope as an antibody having the VH and VL regions shown in FIG. 9a.

The K121-like antibody preferably comprises the CDR loops (CDR1, CDR2 and CDR 3) of the K121 antibody as shown in FIG. 9a. The K121-like antibody may comprise the VH and VL genes of the K121 antibody as shown in FIG. 9a.

K121-like antibodies may be identified by their ability to compete with K121 (or chimaeric or humanised forms of K121) in binding to KMA on HMy2 cells. In this procedure, K121 may be conjugated with biotin using established procedures (Hofmann K, et al. (1982) Biochemistry 21: 978-84). K121-like antibodies are then evaluated by their capacity to compete with the binding of biotinyolated K121 to KMA on HMy2 cells. The binding of biotinylated K121 to HMy2 cells may be assessed by the addition of fluorescein-labelled streptavidin which will bind to biotin on K121 molecules. Fluorescence staining of cells is then quantified by flow cytometry, and the competitive effect of the K121-like antibody expressed as a percentage of the fluorescence levels obtained in the absence of the competitor.

For the purposes of this invention, the term "antibody", unless specified to the contrary, includes bivalent fragments of whole antibodies that retain their binding activity for a target antigen. Such fragments include, for example, $F(ab')_2$ fragments.

In a preferred embodiment of the present invention, the K121-like antibody is a recombinant or monoclonal antibody. In a further preferred embodiment the antibody is a chimaeric or humanized antibody.

When used in the methods of the present invention, the K121-like antibody is not conjugated to a toxin or cytolytic agent. By "toxin" we mean any toxin known in the art such as ricin, saprin, diptheria toxin and *Pseudomonas* exotoxin. By "cytolytic agent" we mean an agent such as melittin that causes lysis of cells.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Monoclonal Antibodies

Monoclonal antibodies directed against KMA epitopes can be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against KMA epitopes can be screened for various properties; i.e. for isotype and epitope affinity.

Mouse-derived monoclonal antibodies can be used for both direct in vivo and extracorporeal immunotherapy. However, it has been observed that when mouse-derived monoclonal antibodies are used in humans as therapeutic agents, the patient produces human anti-mouse antibodies. Thus, mouse-derived monoclonal antibodies are not preferred for therapy, especially for long term use. With established genetic engineering techniques it is possible, however, to create chimaeric or humanized antibodies that have animal-derived and human-derived portions. The animal can be a mouse or another rodent such as a rat.

If the variable region of the chimaeric antibody is mouse-derived while the constant region is human-derived, the chimaeric antibody will generally be less immunogenic than a "pure" mouse-derived monoclonal antibody. These chimaeric antibodies would likely be more suited for therapeutic use, should it turn out that "pure" mouse-derived antibodies are unsuitable.

Chimaeric Antibodies

Methodologies for generating chimaeric antibodies are available to those in the art. For example, the light and heavy chains can be expressed separately, using, for example, immunoglobulin light chain and immunoglobulin heavy chains in separate plasmids. These can then be purified and assembled in vitro into complete antibodies; methodologies for accomplishing such assembly have been described. See, for example, Scharff, M., Harvey Lectures 69:125 (1974). See also Oi et al., Bio Techniques 4(4):214-221 (1986); and Sun et al. Hybridoma 5 (1986) Suppl 1:517-20. Such a DNA construct may comprise DNA encoding functionally rearranged genes for the variable region of a light or heavy chain of a K121-like antibody linked to DNA encoding a human constant region. Lymphoid cells such as myelomas or hybridomas transfected with the DNA constructs for light and heavy chain can express and assemble the antibody chains.

In vitro reaction parameters for the formation of IgG antibodies from reduced isolated light and heavy chains have also been described. See, for example, Beychok, S., Cells of Immunoglobulin Synthesis, Academic Press, New York, p. 69, 1979. Co-expression of light and heavy chains in the same cells to achieve intracellular association and linkage of heavy and light chains into complete $H_2L_2$ IgG antibodies is also possible. Such co-expression can be accomplished using either the same or different plasmids in the same host cell.

Humanised Antibodies

In another preferred embodiment of the present invention the K121-like antibody is humanised, that is, an antibody produced by molecular modeling techniques wherein the human content of the antibody is maximised while causing little or no loss of binding affinity attributable to the variable region of the murine antibody.

The methods described below are applicable to the humanisation of K121-like antibodies. A two-step approach may be used which involves (a) selecting human antibody sequences that are used as human frameworks for humanization, and (b) determining which variable region residues of the animal monoclonal antibody should be selected for insertion into the human framework chosen.

The first step involves selection of the best available human framework sequences for which sequence information is available. This selection process is based upon the following selection criteria.

(1) Percent Identities

The sequences of the heavy and light chain variable regions of an animal monoclonal antibody that is to be humanised are optimally aligned and compared preferably with all known human antibody heavy and light chain variable region sequences.

Once the sequences are thus compared, residue identities are noted and percent identities are determined. All other factors being equal, it is desirable to select a human antibody which has the highest percent identity with the animal antibody.

(2) Sequence Ambiguities

In cases where sequences are derived by direct protein sequencing, the known human antibody chain sequences may be evaluated for the presence of unidentified residues and/or ambiguities, which are sequence uncertainties. The most common of such uncertainties are mistaken identification of an acidic amino acid for an amide amino acid due to loss of ammonia during the sequencing procedure, eg., incorrect identification of a glutamic acid residue, when the residue actually present in the protein was a glutamine residue. All other factors being equal, it is desirable to select a human antibody chain having as few such ambiguities as possible.

(3) Pin-Region Spacing

Antibody chain variable regions contain intra-domain disulfide bridges. The distance (number of residues) between the cysteine residues comprising these bridges is referred to as the Pin-region spacing (Chothia et al, J. Mol. Biol. 196:901 (1987)). All other factors being equal, it is most desirable that the Pin-region spacing of a human antibody selected be similar or identical to that of the animal antibody. It is also desirable that the human sequence Pin-region spacing be similar to that of a known antibody 3-dimensional structure, to facilitate computer modeling.

Based upon the foregoing criteria, the human antibody (or antibodies) having the best overall combination of desirable characteristics is selected as the framework for humanisation of the animal antibody. The heavy and light chains selected may be from the same or different human antibodies.

The second step in the methods of this invention involves determination of which of the animal antibody variable region sequences should be selected for grafting into the human framework. This selection process is based upon the following selection criteria:

(1) Residue Selection

Two types of potential variable region residues are evaluated in the animal antibody sequences, the first of which are called "minimal residues." These minimal residues comprise CDR structural loops plus any additional residues required, as shown by computer modeling, to support and/or orient the CDR structural loops.

The other type of potential variable region residues are referred to as "maximal residues." They comprise the minimal residues plus any additional residues which, as determined by computer modeling, fall within about 10 Å of CDR structural loop residues and possess a water solvent accessible surface (Lee et al, J. Biol. Chem. 55:379 (1971)).

(2) Computer Modeling

To identify potential variable region residues, computer modeling is carried out on (a) the variable region sequences of the animal antibody that is to be humanised, (b) the selected human antibody framework sequences, and (c) all possible recombinant antibodies comprising the human antibody framework sequences into which the various minimal and maximal animal antibody residues have been grafted.

The computer modeling is performed using software suitable for protein modeling and structural information obtained from an antibody that (a) has variable region amino acid sequences most nearly identical to those of the animal antibody and (b) has a known 3-dimensional structure. An example of software that can be used is the SYBYL Biopolymer Module software (Tripos Associates). The antibody from which the structural information can be obtained may be but need not necessarily be a human antibody.

Based upon results obtained in the foregoing analysis, recombinant chains containing the animal variable regions producing a computer modeling structure most nearly approximating that of the animal antibody are selected for humanisation.

Wholly human antibodies can be made by using human immunoglobulin expression libraries (Stratagene Corp., La Jolla, Calif.) to produce fragments of human antibodies ($V_H$, $V_L$, $F_V$, Fd, Fab, or $F(ab')_2$), and using these fragments to construct whole human antibodies using techniques similar to those for producing chimaeric antibodies.

Modes of Administration

K121-like antibodies may be administered directly to a subject in need of treatment for multiple myeloma.

The growth of tumour cells may be inhibited or reduced by administering to a subject in need of the treatment an effective amount of a K121-like antibody. Typically, the antibody may be administered in an amount of about 0.001 to 2000 mg/kg body weight per dose, and more preferably about 0.01 to 500 mg/kg body weight per dose. Repeated doses may be administered as prescribed by the treating physician. However, other amounts are also suitable. Generally, the administration of the antibody is conducted by infusion so that the amount of antibody present that may produce a detrimental effect may be kept under control by varying the rate of administration. Typically, the infusion of one dose may last a few hours. However, also contemplated herein is the constant infusion of a dose for therapeutic purposes that will permit the maintenance of a constant level of the antibody in serum. The infusion of the K121-like antibody may be conducted as follows. Intravenous (I.V.) tubing may be pretreated, e.g., with 0.9% NaCl and 5% human serum albumin and placed for intravenous administration. The I.V. infusion may comprise a total volume of 250 ml of 0.9% NaCl and 5% human serum albumin and be infused over a period of about 2 hours depending on any rate-dependent side effects observed. Vital signs should be taken, for example, every fifteen minutes during the infusion and every one hour post infusion until stable. A thorough cardiopulmonary-physical examination may be done prior to, and at the conclusion, of the infusion. Medications including acetaminophen, diphenhydramine, epinephrine, and corticosteroids may be kept at hand for treatment of allergic reactions should they occur. The administration of the antibody may be repeated as seen desirable by a practitioner.

As will be appreciated by those skilled in the art, some myeloma patients have significant levels of free kappa light chain in their circulation. As K121-like antibodies react with free kappa light chains, their presence in the fluid of the subject may reduce the efficiency of the treatment. Accordingly, in a preferred embodiment of the invention the method of treatment further comprises the step of treating the subject to reduce the levels of free kappa light chains circulating in the fluid (e.g. blood) of the subject prior to administration of the K121-like antibody. This additional treatment step may involve, for example, plasmapherisis. As will be known by those skilled in the art, plasmapherisis is a process in which the plasma is removed from blood cells by a device known as a cell separator. The separator works either by spinning the blood at high speed to separate the cells from the fluid or by passing the blood through a membrane with pores so small that only the plasma can pass through. The cells are returned to the subject, while the plasma, which contains the free kappa light chains, is discarded and replaced with other fluids. Medication to keep the blood from clotting (e.g. an anticoagulant) may be given through a vein during the procedure.

K121-like antibodies are also applicable to the purging of malignant plasma cells from biological samples, be it fluid or tissue samples. The purging of myeloma cells from a fluid sample is part of the invention and may be practiced by contacting a biological fluid suspected of comprising malignant plasma cells with a K121-like antibody that is capable of selectively binding to and causing apoptosis of the malignant cells. This method may be utilized for purging unwanted cells ex vivo by extracting a biological sample from a patient, eliminating the malignant cells by apoptosis induced by K121-like antibodies and then replenishing the purged sample to the patient.

It will be appreciated that methods of treating multiple myeloma involving the use of a K121-like antibody may be performed in isolation or as an adjunct to known chemotherapy or radiotherapy regimes. For example, K121-like antibody treatment may be conducted in conjunction with or after treatment with drugs such as melphalan or cyclophosphamide.

In order that the present invention may be more clearly understood preferred forms will be described with reference to the following non-limiting examples.

EXAMPLE 1

Assessment of Cytotoxicity

Cytotoxic activity of mAb K121 was evaluated using the Cyto Tox96 Non-Radioactive Cytotoxicity Assay Kit (Promega) which measures lactate dehydrogenase (LDH) released into the supernatant by cells during cell lysis. HMy2 (KMA positive) and K562 (KMA negative) cells were harvested from stock cultures and resuspended at $1\times10^6$ cells/ml in 2×RPMI supplemented with 5% FBS. Aliquots of $3\times10^4$ cells were added to individual wells of a 96 well tissue culture plate. K121 mAb, at concentrations of 2.5, 5.0, 7.5, 10, 12.5 µM, was added in a volume of 30 µl to appropriate wells in duplicates. After 20 h incubation at 37° C. in an atmosphere of 5% $CO_2$, the supernatant from each well was collected and centrifuged at 3000 g for 1 min. Clarified supernatant (50 µl) was transferred to another 96 well microtitre assay plate and mixed with an equal volume of substrate. The plate was incubated at room temperature in the dark for 30 min and the reaction stopped with 50 µl stop solution. Absorbance values were measured on an Organon Teknika microelisa plate reader (Turnhout, Belgium) at 492 nm. Culture medium (1×RPMI supplemented with 2.5% FBS) alone was included as a background control because FBS and phenol red in the medium can result in apparent elevated LDH levels. For time course studies, HMy2 cells were incubated with 12.5 µM of K121 mAb and the culture supernatant was harvested at 4, 8, 12, 16 and 20 hours after addition of the antibody.

EXAMPLE 2

Apoptosis Assays

The mechanism of the cytoxic activity of K121 on HMy2 cells was evaluated in 2 ways, Annexin V binding and the TUNEL assay. A parallel LDH assay was carried out during both assays to confirm that cell death occurred.

Annexin V Binding. AnnexinV is a protein that binds specifically to phosphotidyl-serine in the cell membrane. Binding occurs once the membrane has started to break down and the phospholipid "flips out" into the extracellular media. As a result this method measures the earliest stage of apoptosis. The Annexin V binding method is described briefly. HMy2 cells were harvested from stock cultures and resuspended in 1×RPMI supplemented with 5% FBS to a density of $1\times10^6$ cells/ml. Five hundred microliter aliquots of cells were added into a 6 well tissue culture plate. An equal volume of K121 mAb at a concentration of 10.7 µM was added to the cells and the assay tray incubated at 37° C. in an atmosphere of 5% $CO_2$. For the negative control, an equal volume of PBS was added. Cells were harvested by centrifugation from the wells at t=16 and 20 h. An aliquot of the supernatant was assayed for extracellular LDH and the cell pellet was washed in binding buffer (10 mM HEPES, 140 mM NaCl and 2.5 mM $CaCl_2.2H_2O$). Washed cells were resuspended in 100 µl of binding buffer and incubated with 2 µl of annexin V-FITC (Bender MedSystems, Vienna, Austria) for 15 min at room temperature. An additional 400 µl of binding buffer was added and the cells counter stained with 1 µl of 1 mg/ml propidium iodide (Sigma-Aldrich, St Louis, Mich.) on ice for 15 min. The cells were then analysed by flow cytometry using a FACScan (BD).

TUNEL Assay. In the final stages of apoptosis, the chromosomal DNA undergoes a characteristic pattern of fragmentation. The TUNEL assay relies on a terminal transferase enzyme to label the 3' ends of the fragmented DNA. Therefore, this assay is a measure of the final stages of apoptosis. In brief, duplicate wells containing HMy2 cells in the presence of K121/or PBS were setup and incubated as described in the previous section. The TdT-mediated dUTP nick-end labelling (TUNEL) assay was performed using the Apoptosis Detection System Fluorescein (Promega, Madison, Wis.). Cells were prepared and the assay performed as described by the manufacturers. Briefly, the cells were washed in PBS and fixed with 10% formaldehyde followed by 70% alcohol. Intracellular DNA was enzymatically labelled with fluorescein-12-dUTP at the 3' end and analysed on the FACScan.

EXAMPLE 3

SCID Mouse Tumour Model

In order to evaluate the potential anti-tumour effects of K121 in vivo, 6 week-old SCID mice were injected intraperitoneally (i.p.) on day 0 with HMy2 cells. Subsequent to the injection of tumour cells, mice were administered either K121 antibody or PBS by i.p. injection. As HMy2 cells secrete human IgG, the progression of tumour growth was monitored by quantification of human IgG in the serum of recipient mice using a human IgG-specific immunoassay.

EXAMPLE 4

Quantitation of Human IgG

An enzyme linked immunosorbent assay (ELISA) was used to quantify the levels of human IgG in the sera of SCID mice. Protein A in PBS-Az (50 µl/well of 100 µg/ml) was incubated in a 96 well ELISA plate at 37° C. for 1 hour. The wells were washed 3 times with PBS-Az and non-specific binding sites were blocked with 3% BSA in PBS-Az at 37° C. for 1 hour. The wells were washed twice in PBS-Az and incubated at 37° C. for 1 hour with 50 µl/well of mouse serum diluted 2.5 fold with 1% BSA in PBS-Az. Following 3 washes with PBS-Az, the bound antibodies were detected with 50 µl/well of goat anti-human κ-light chain AP conjugated (1:1000 dilution in 1% BSA-PBS-Az) at 37° C. for 1 hour. The bound antigen-antibody complexes were visualized by the addition of p-nitrophenyl phosphate (pNPP) substrate (50 µl/well at 1 mg/ml) in ELISA substrate buffer (0.1M glycine, 1 mM $MgCl_2$, 1 mM $ZnCl_2$, pH10.4) following 2 washes in PBS-Az, one in MilliQ water and one in ELISA substrate buffer. Colour was developed at room temperature for 10 min and the reaction was stopped by the addition of 3M NaOH (50 µl/well). Absorbance was determined at 405 nm using an Organon Teknika microelisa plate reader (Turnhout, Belgium).

For the quantification of human IgG, a standard curve was included in the assay. Mouse serum was replaced with serial dilutions of purified human IgG1 kappa (6 µg/ml-6 ng/ml; Serotec Ltd, Oxford, England).

EXAMPLE 5

Incubation with K121 Results in the Death of Antigen-Bearing Cells

Incubation of HMy2 and K562 cells with K121 revealed that the mAb induces specific target cell death in both a time and concentration dependant manner (FIG. 1). The cytotoxic activity of K121 was first detected approximately 12 hr after addition to the target cell culture and the level of cell death increased over the following 8 hrs. The cytotoxic effect of K121 was maximal at a final concentration of 3.6 µM with significant cytotoxicity being detected at 2.5 µM. The observed cytotoxic activity of K121 occurred in the absence of added accessory effector cells or serum components (ie. complement).

HMy2 cells incubated in the presence or absence of K121 were observed at 200× magnification under an inverted light microscope. Concurrent studies of HMy2 cells incubated with a scFv-mel immunotoxin (Dunn, R D. et al., (1996) Immunotechnology 2: 229) were carried out. Cells incubated with K121 Mab showed signs of cell shrinkage and membrane "blebbing". By contrast the scFv-mel caused clumping of the cells and membrane lysis.

Flow cytometric analysis of K121 treated HMy2 cells showed an increase in 90° light scatter properties compared to untreated cells (FIG. 2) which reflects an increase in internal granularity and chromatin condensation in the antibody treated cells. There was a concomitant decrease in forward light scatter properties of antibody treated cells which is indicative of cell shrinkage. The combination of increased granularity, chromatin condensation and cell shrinkage exhibited by the K121 treated cells suggested that these cells were dying as a result of induction of apoptosis.

EXAMPLE 6

The Interaction of K121 with Target Cells Induces Apoptosis

Figure 3A:
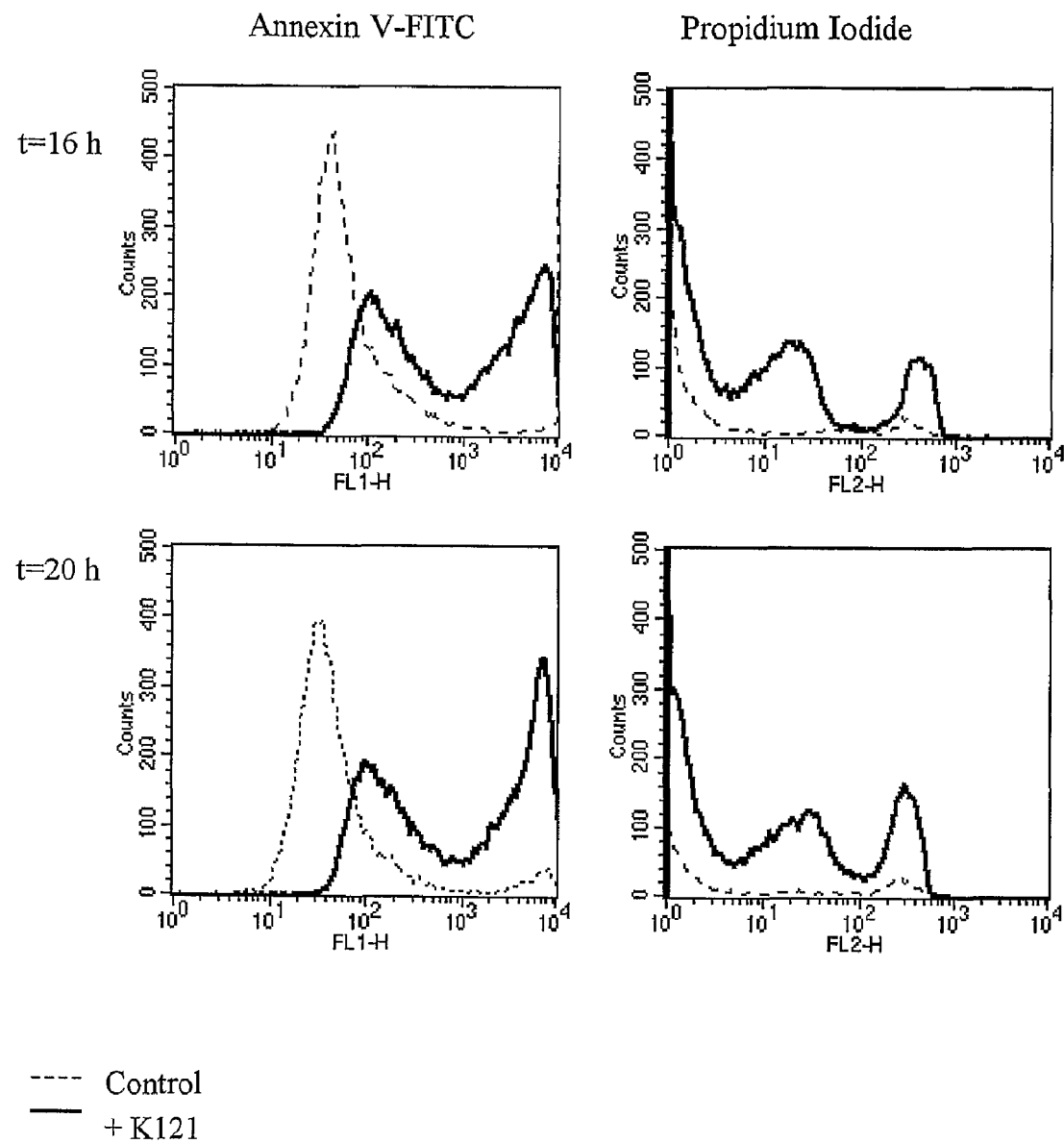
FIG. 3(a) Flow cytometric analysis of K121-induced apoptosis of HMy2 cells using annexin V-FITC. HMy2 cells were incubated in the absence (Control) or presence of K121 at 37° C. for 16 h or 20 h. Afterwards, the cells were incubated with annexin V-FITC and counter-stained with propidium iodide. (b). Cytotoxicity of K121 mAb on HMy2 cells carried out in parallel with the AnnexinV assay. HMy2 cells were incubated at 37° C. for 16 or 20 h in the absence (control) or presence (5.35 µM) of K121 mAb. Culture supernatant was harvested for analysis of cytosolic LDH leakage.
Figure 3B:
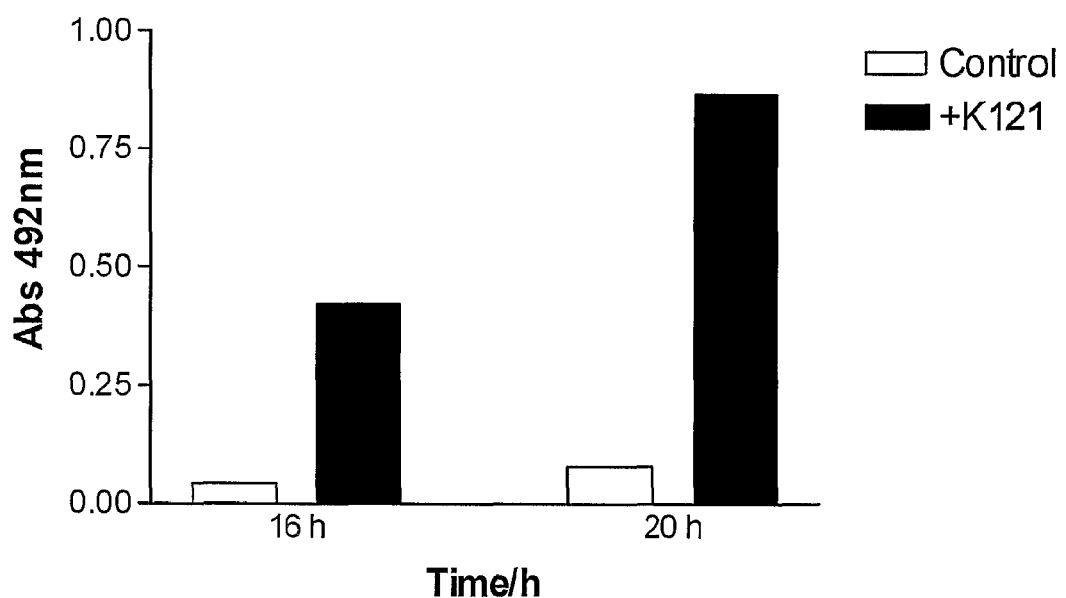

Two independent assay systems were used to determine the mechanism by which K121 kills antigen-bearing cells. Early stage apoptosis was assessed by the binding of annexin V to K121 treated cells. Immunofluorescence staining with annexin V-FITC revealed increasing numbers of positively stained HMy2 cells 16 and 20 hrs after initiating treatment with K121 compared to non-antibody treated cells (FIG. 3a). The increasing percentage of annexin V stained cells correlated with increased proportion of dead cells as determined by staining with propidium iodide (FIG. 3a) and leakage of LDH (FIG. 3b).

Figure 4A:
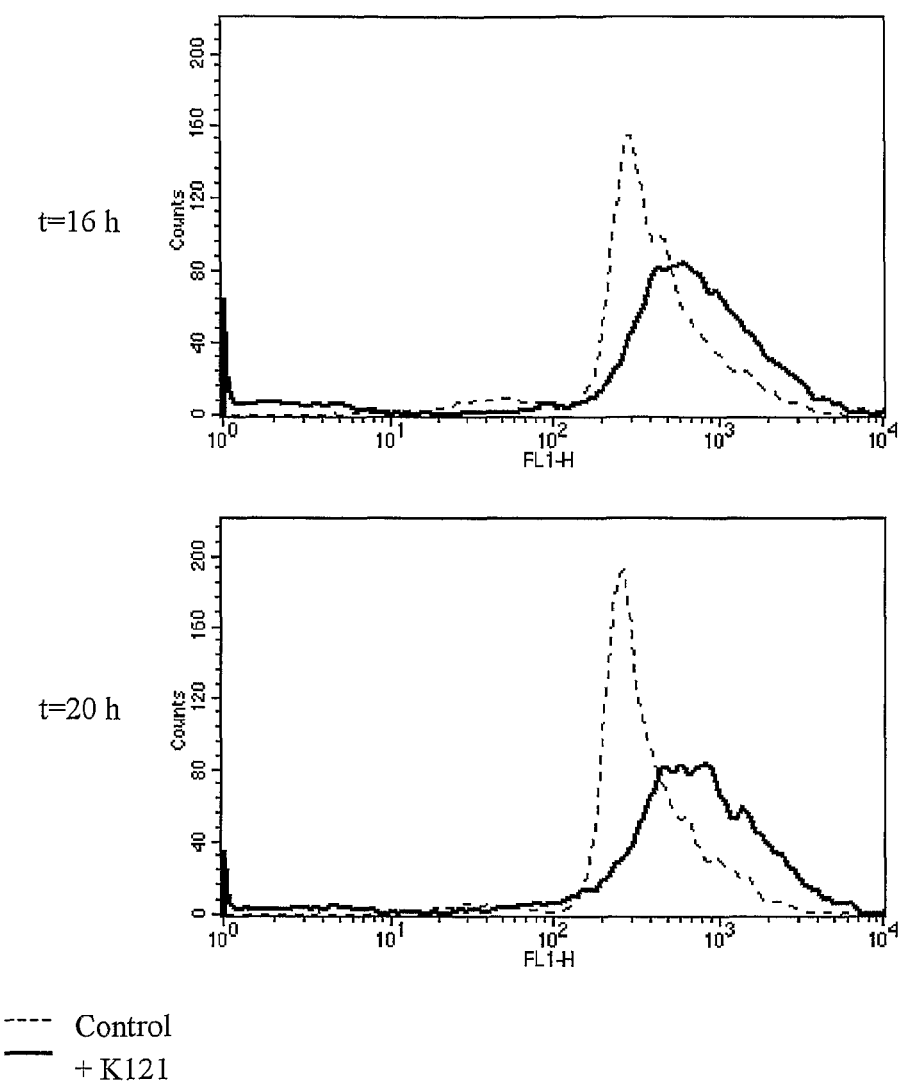
FIG. 4 (a) Flow cytometric analysis of K121-induced apoptosis of HMy2 cells using the TUNEL assay. HMy2 cells were incubated in the absence (Control) or presence of K121 at 37° C. for 16 h or 20 h. Afterwards, the cells were fixed and intracellular DNA enzymatically labelled with Fluorescein-12-dUTP at the 3' end. (b) Cytotoxicity of HMy2 cells after 16 and 20 hours incubation with and without K121 carried out in parallel with the TUNEL assay. HMy2 cells were incubated at 37° C. for 16 or 20 h in the absence (control) or presence (5.35 µM) of K121 mAb. Culture supernatant was harvested for analysis of cytosolic LDH leakage.
Figure 4B:
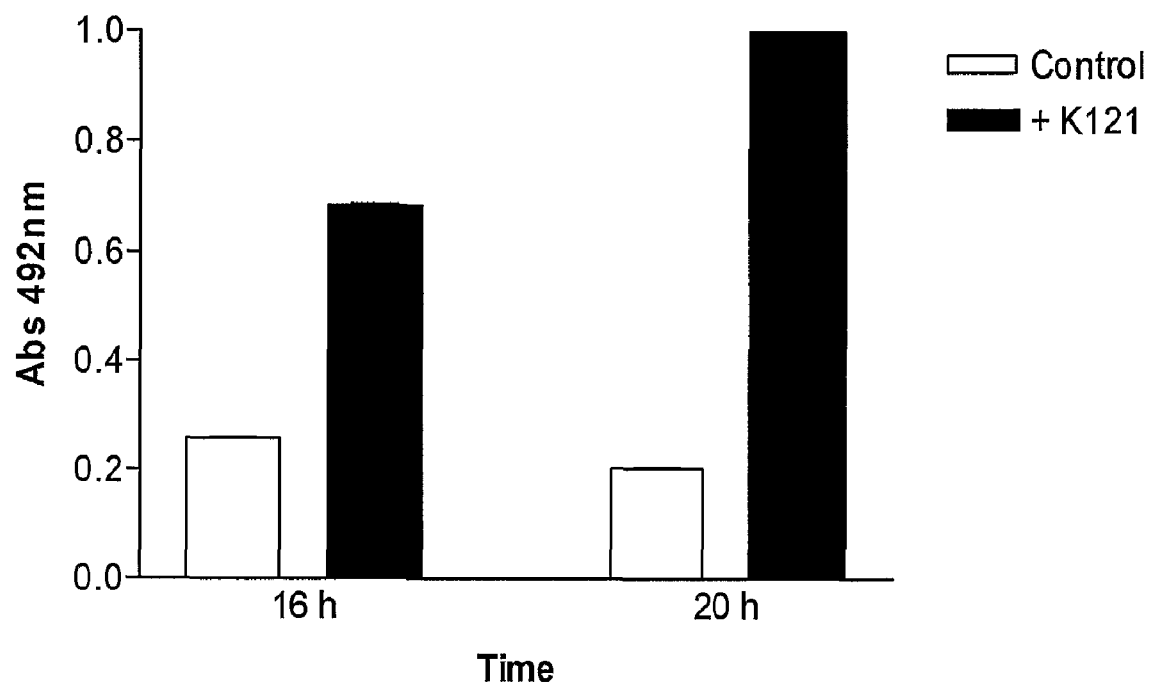

Analysis of DNA fragmentation, a late stage process in apoptosis, was assessed using the TUNEL method. The shift in fluorescence observed in HMy2 cells incubated with K121 was significant after 16 and 20 hours incubation when compared to untreated cells (FIG. 4a) and is typical of the DNA fragmentation pattern associated with apoptosis. Once again, the measurement of apoptosis correlated with increasing numbers of dead cells as determined by leakage of LDH (FIG. 4b). When taken together these data show that K121 treated cells are undergoing apoptosis.

EXAMPLE 7

K121 Prevents the Growth of HMy2 Tumour Cells in Mice

SCID mice that had received $10^7$ HMy2 cells on day 0 were administered either 3 consecutive doses of K121 (1.25 mg each) (n=6) or scFv-mel (0.5 mg each) (n=7) on days 1,2 and 3 or PBS (1.25 mg each) (n=6) as a treatment control. Blood samples were taken before administration of the tumour cells and at weekly intervals post injection of tumour cells, and the growth of HMy2 cells was monitored by the appearance of human IgG in the serum of the animals. In the PBS-treated control mice, human IgG was detected in the serum of 6/6 animals (FIG. 5a) with the time for initial detection of human IgG ranging from 3 weeks to 8 weeks post injection of tumour cells. Similarly, mice treated with an immunotoxin comprising the cytolytic peptide melittin linked to a K121 scFv fragment (scFv-mel) showed elevated human IgG levels 3 weeks after injection of cells (FIG. 5b). By contrast, human IgG was not detected in the serum of K121-treated animals over the same period (FIG. 5c). In general, the PBS and scFv-mel treated animals exhibited abdominal swelling, became lethargic and, after 9 weeks, 5/6 mice had died. Mice treated with K121 did not display these symptoms and all were alive at week 9, at which time one mouse from this group, together with the surviving animal from the control group, was sacrificed and dissected. The K121 treated animal had no gross organ abnormalities. The untreated animal, however, had a large tumour mass in the abdominal cavity, an enlarged spleen and wasting of the lungs. Tissue samples from both animals are currently being examined by immunocytochemical techniques for HMy2 infiltration. These studies clearly demonstrated that K121 alone is capable of preventing growth of human lymphoblastoid tumour cells in an immunodeficient (SCID) mouse model.

In a second example, SCID mice that were injected with $10^7$ HMy2 cells on day 0 received varying dosage levels of K121 on days 1, 2 and 3 as follows:

Group 1; PBS control (n=6)
Group 2; 1.0 mg K121 per dose. Total antibody dosage, 3.0 mg (n=6)
Group 3; 0.5 mg K121 per dose. Total antibody dosage, 1.5 mg (n=6)
Group 4; 0.1 mg K121 per dose. Total antibody dosage, 0.3 mg (n=6)
Group 5; 0.05 mg K121 per dose. Total antibody dosage, 0.15 mg (n=6)

Tumour progression was monitored by quantification of human IgG in the serum of the mice.

Figure 6:
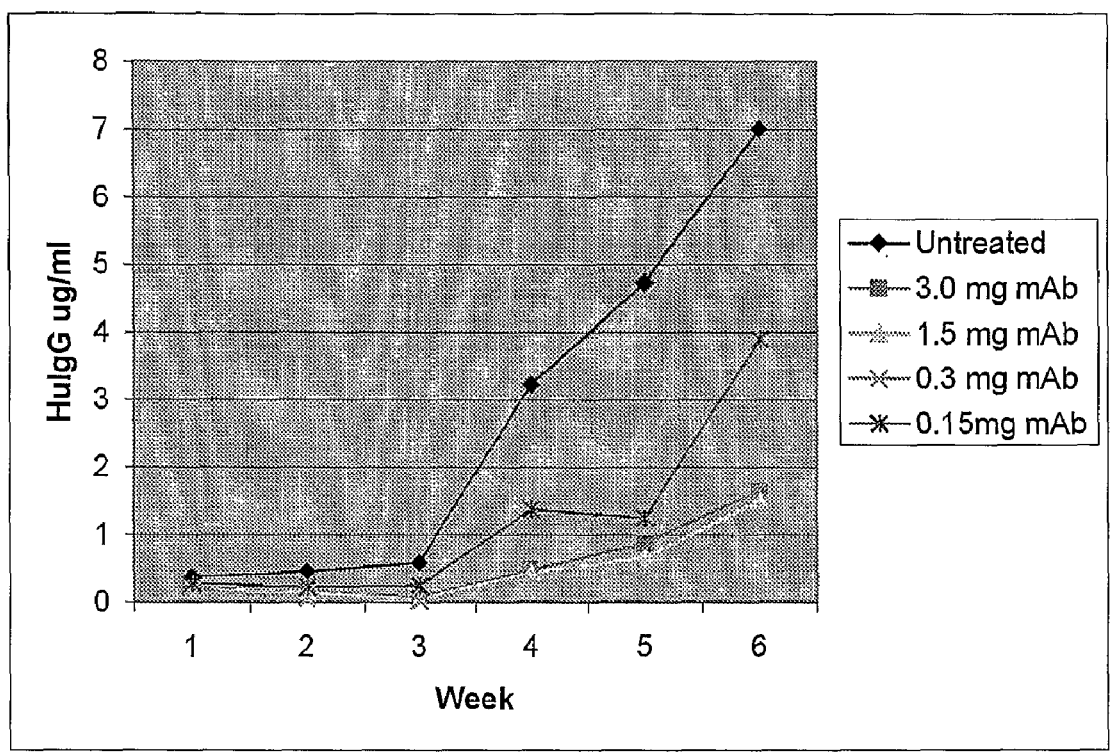
FIG. 6. Effect of antibody treatment on tumour growth in SCID mice. SCID mice injected with HMy2 cells on day 0 and K121 Mab administered over 3 days (day 1, 2 and 3) at total dose levels of 3.0, 1.5, 0.3, 0.15 and 0 (PBS control) mg. Tumour growth was assessed by quantification of human IgG in mouse serum. Values plotted are means from 6 mice, except for the Week 6 value in the untreated group, where the value is from a single mouse.
Figure 7:
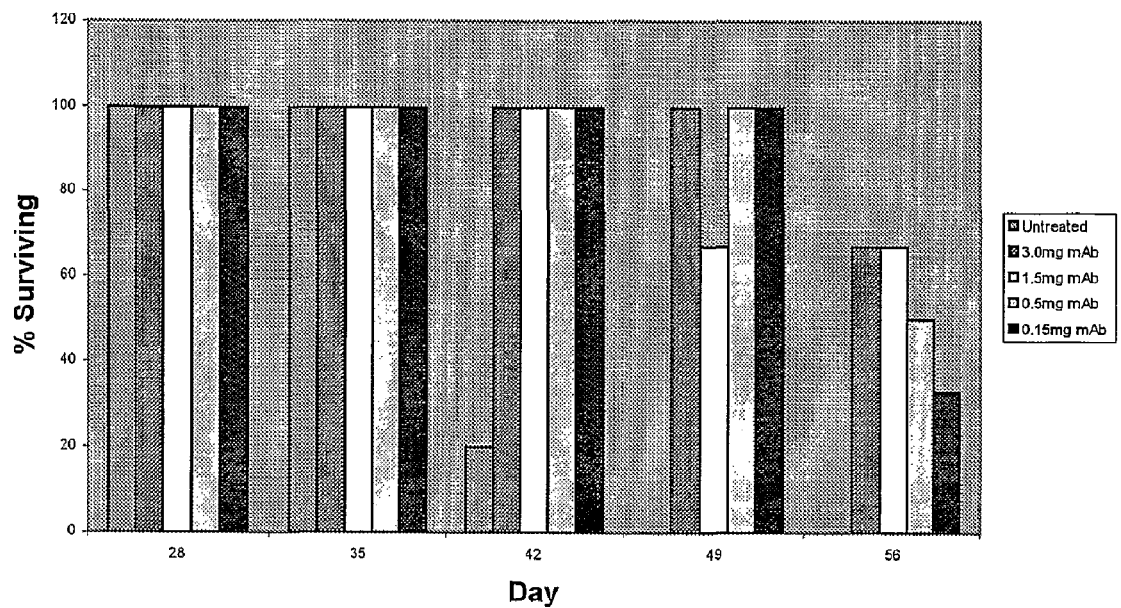
FIG. 7. Effect of antibody dose on survival of tumour-bearing mice.
Figure 8:
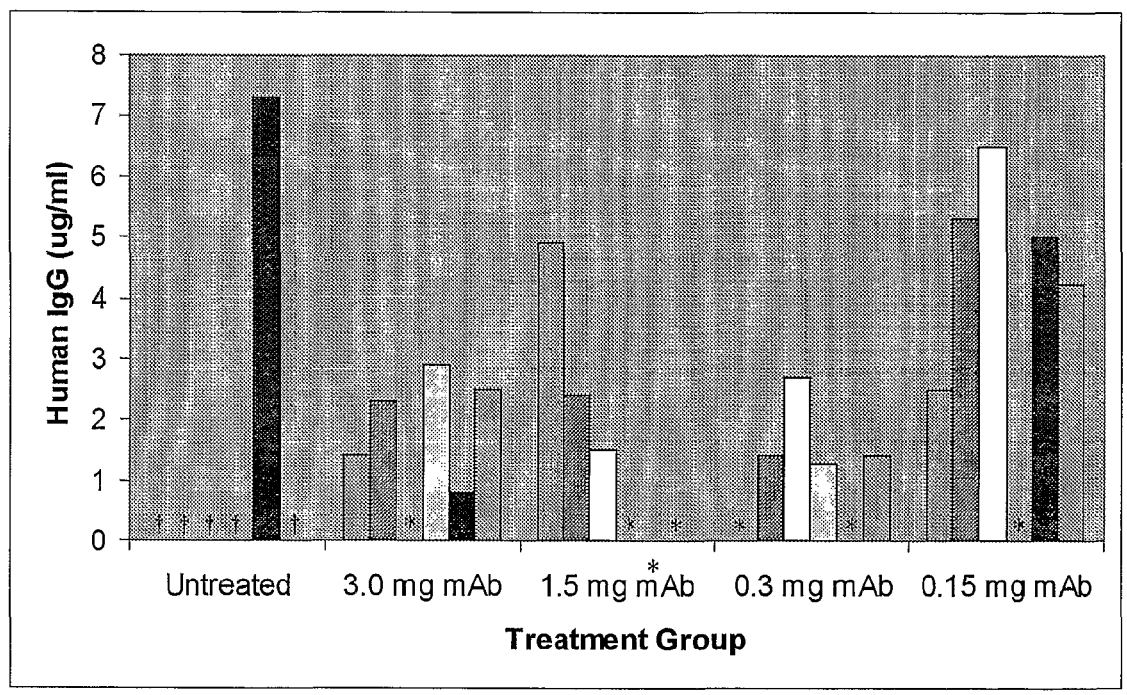
FIG. 8. Human IgG levels in the serum of untreated and antibody-treated mice 42 days after injection of tumour cells. Values are for individual mice. *Human IgG not detectable; † mortalities FIG. 9. (a) The amino acid sequence and corresponding DNA sequence for the K121 heavy chain (VH) and light chain (VL) variable regions. The CDR regions are shown in bold type. (b) Overlapping oligonucleotides (VH1-VH6) derived from the VH gene of K121. (c) Overlapping oligonucleotides (VL1-VL6) derived from the VL gene of K121. (d) PCR primers for oligonucleotide extension of K121 VH. (e) PCR primers for oligonucleotide extension of K121 VL. (f) Schematic representation of a method for creating the K121 monoclonal antibody heavy and light chain variable regions using oligonucleotide extension.

All untreated mice developed elevated levels of human IgG by day 28 (FIG. 6) and the majority (4/5) of this group died by day 42 (FIG. 7). Postmortem examination revealed enlarged spleens and macroscopic tumours in liver and kidney. Tumour bearing mice treated with K121 showed either delayed onset of tumour progression or complete absence of tumour growth as indicated by levels of human IgG in serum (FIGS. 6 and 8) and postmortem examination upon termination of the experiment at day 56. Across the 4 treatment groups 7 of 24 mice showed undetectable levels of human IgG in their serum at day 42 (FIG. 8). Six of these mice showed no gross signs of tumour growth at postmortem examination on day 56. All untreated mice died or were euthanased for ethical reasons by day 49, while 13/24 mice in the antibody treatment groups survived until day 56 (FIG. 7).

In summary, tumour-bearing mice responded to K121 treatment in a dose dependent manner. Complete absence of tumour growth at day 42 was apparent in 30% of mice, with this effect being most pronounced in the mice receiving a total dosage of 1.5 mg K121 (FIG. 8). Tumour growth was rapid and aggressive in untreated mice, with 100% mortality by day 49 (FIG. 7). At this time point, the combined treatment groups showed mortality of less than 10%.

EXAMPLE 8

Synthesis of a K121 Like Antibody by Oligonucleotide Assembly Using PCR

An example of the strategy used to create a monoclonal antibody by extension of synthetic oligonucleotides using the PCR has previously been described in the literature (Sato et al. (1994) Molecular Immunology 31 (5): 371). In order to create a K121 like monoclonal antibody from the published DNA sequence (as shown in FIG. 9a) the VH gene may be divided into six overlapping oligonucleotides VH1-VH6 (FIG. 9b). Likewise the K121 VL gene may be divided into six overlapping oligonucleotides VL1-VL6 (FIG. 9c). Three of the VH oligonucleotides would have the sense DNA sequence (FIG. 9d, VH1, 3 and 5) and three would have the anti-sense DNA sequence (FIG. 9d, VH2, 4 and 6). Similarly, three of the VL oligonucleotides would have the sense DNA sequence (FIG. 9e, VL1, 3 and 5) and three would have the antisense DNA sequence (FIG. 9e, VL2, 4 and 6).

Figure 9F:
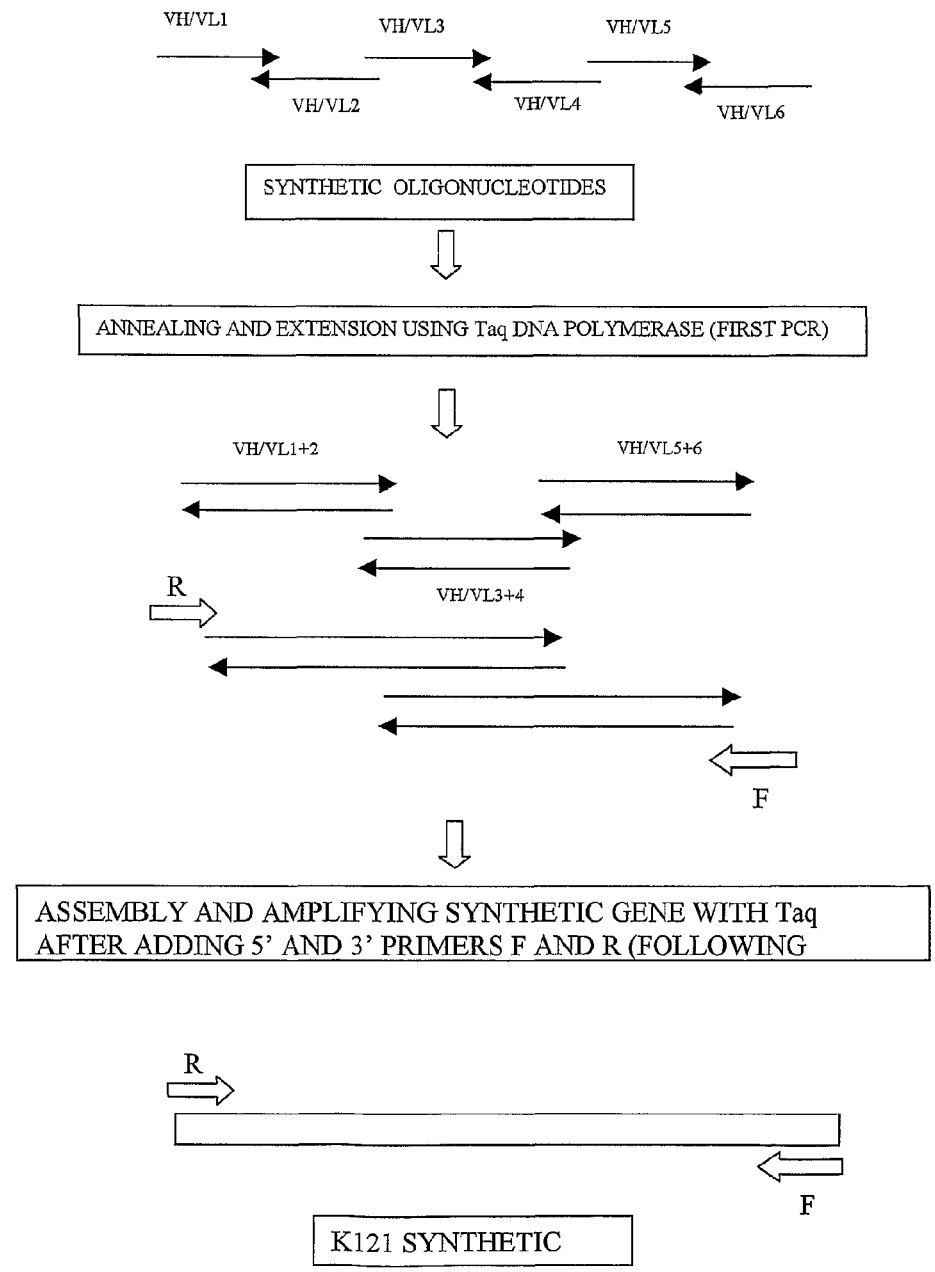

The first PCR using a Taq polymerase would assemble the three sets of oligonucleotides to produce three double stranded DNA fragments (FIG. 9f). The three products of the first amplification would then be gel extracted and the isolated DNA fragments would be used as templates for assembling the full gene sequence using a Taq polymerase. In the final assembly of the VH gene a PCR primer complementary to the 5' region of the gene (VHF) and an antisense primer complementary to the 3' region of the gene (VHR) would be used to create the complete K121 VH gene sequence. Similarly PCR primers to the 5' (VLF) and 3' (VLR) regions of the VL gene should be used for amplification of the complete K121 VL gene. The final gene products should be sequenced to confirm the presence and fidelity of the full V genes.

The synthesised K121 VH and VL genes should then be ligated into a mammalian expression vector containing the relevant murine Ig constant region genes; Cγ1 for the heavy chain and Cκ for the light chain. A mammalian cell line should then be transfected with the resulting vectors and the expression of functional K121 should be monitored by immunoassay as described for the chimaeric antibody.

EXAMPLE 9

Construction of the Chimaeric Antibody, cK121

Isolation of K121 VH and VL Genes

The variable region genes of the heavy chain (K121 VH) and the light chain (K121 VL) of the monoclonal antibody, K121, were isolated by PCR. The template for amplification of the VH and VL gene was the scFv-mel gene construct. PCR primers (FIG. 10) used for amplification were designed to introduce compatible restriction sites for directional cloning into the mammalian expression vectors pCMV-γ1 and pCMV-KR (Mahler et al., (1997) Immunotechnology 3:31).

The products of the PCR amplification were separated by electrophoresis on a 1% agarose gel and the DNA bands of the expected size were extracted using a QIAquick gel extraction kit (Qiagen, Germany). The isolated gene fragments were then ligated into the pGEM-T vector and transformed into competent bacterial cells, JM109 (Promega, USA). After overnight incubation, PCR screening using vector specific primers (M13) identified the colonies containing an insert. Positive clones of VH and VL were chosen and plasmid DNA was prepared using the Wizard Mini-prep kit (Promega, USA). Two clones representing VH and VL were sequenced on an ABI automated DNA sequencer by Sydney University Prince Alfred Macromolecular Analysis Centre (SU-PAMAC). The DNA sequences of K121 VH and VL were identical to those shown in FIG. 9a with the additional restriction enzyme sites and nucleotides incorporated in the PCR primers (FIG. 10).

Ligation of K121 VH and VL into the Expression Vector

The genes for K121 VH and VL were restricted from pGEM-T clones using the restriction enzymes Bam HI and ApaLI. Restricted VH and VL inserts were purified by gel extraction. A leader sequence for the heavy and light chains was isolated by restriction of pCMV-γ1 with Apa LI and Hind III followed by gel extraction of the leader sequence insert. The Hind III and Apa LI digested leader sequence was ligated simultaneously with the K121 VH and VL genes into restricted Hind III and Bam Hi pCMV-γ1 and pCMV-KR respectively. After transformation into competent JM109 cells, colonies containing inserts were screened by PCR using the VH and VL gene specific primers. Plasmid DNA was prepared from positive clones and the inserts were confirmed by restriction enzyme digestion with Bam HI and Hind III. At this stage the pCMV-γ1-cVH and pCMV-KR-cVL plasmids should be sequenced using vector specific primers to confirm the correct K121 VH and VL DNA sequence.

Transfection of Expression Plasmids into CHO Cells

CHO-K1 (Chinese Hamster Ovarian) cells were grown in DMEM/F12 medium with 10% FBS (Sigma Aldrich, USA) and incubated at 37° C. in an atmosphere of 5% CO2. A total of 5 μg of the plasmid preparations, pCMV-γ1-cVH and pCMV-KR-cVL, were incubated with $4 \times 10^6$ CHO cells in 200 μl of RPMI medium (Sigma Aldrich, USA) supplemented with 10% FBS and 2 mM L-glutamine (Trace Biosciences, NSW). The cell/DNA mixture was placed in a cuvette and electroporation was carried out in a Gene Pulser (BioRad, USA) at the following settings; resistance 100 ohms, volts 0.3, capacitance Ext 960 μFD and time constant 33-38 msec. Afterwards the cells were transferred to 10 ml of DMEM/F12 medium with 10% FBS and grown for 48 hrs at 37° C. in an atmosphere of 5% $CO_2$. Selection of transfected cells was performed using the neo selection medium containing 400 μg/ml of G418 antibiotic (GENETICIN, Sigma Aldrich, USA) in DMEM/F12. After 3 days the culture supernatant was replaced and the cells were expanded to 150 cm² tissue culture flasks. After 7 days in selection medium the expression of cK121 was assessed by two separate ELISA's.

EXAMPLE 10

Assessment of the Expressed Chimaeric Antibody, cK121

Figure 11:
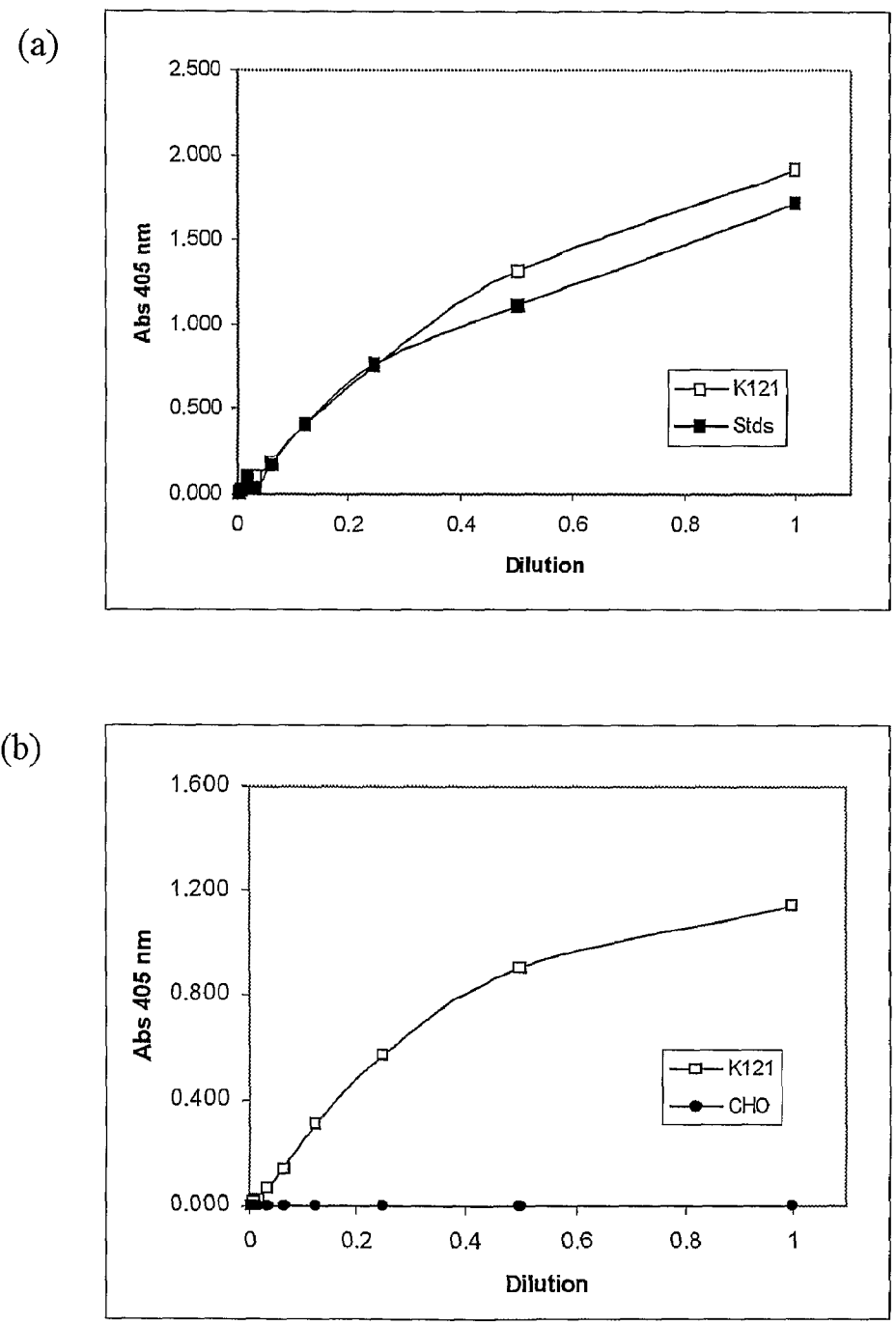
FIG. 11 (a) ELISA for detection and quantitation of human antibody in the transfected CHO cell supernatant. Culture supernatant from the transfected CHO cells was serially diluted and human antibody that bound to the immobilised goat anti-human IgG+A+M was detected with goat anti-human Fc specific AP conjugate. A standard curve was performed in parallel using serial dilutions of human IgG1 κ. Bound antibody was visualised by colour development and absorbance measured at 405 nm. (b) An ELISA for detection of chimaeric K121 binding to human kappa light chain. Culture supernatant from transfected and untransfected CHO cells was serially diluted and antibody that bound to immobilised human kappa light chains was detected using goat anti-human Fc specific AP conjugate. After colour development bound antibody was detected by absorbance at 405 nm.

The procedure for the ELISA was carried out as detailed in Example 4 with some changes in specific reagents. Briefly, to determine expression of a chimaeric antibody containing the human Fc region, an ELISA was performed by coating the wells of a 96 well plate with goat anti-human IgG, IgA and IgM (50 μl/well of 10 μg/ml). Conditioned medium from the transfected CHO cells was then incubated in the wells, followed by a goat anti-human (Fc-specific)-AP conjugate and colour development with the substrate pNPP (Sigma Aldrich, USA). A standard curve for the first ELISA was prepared using serial dilutions of human IgG1 kappa (6 μg/ml-6 ng/ml). In parallel, clarified supernatant from transfected CHO cells was subjected to serial dilution and the samples were analysed (FIG. 11a). A dilution curve similar to the standard curve was obtained for the cK121 expressing CHO cells. The estimated concentration of cK121 in the CHO cell conditioned medium was 6 ng/μl.

A second ELISA was carried out to demonstrate binding of the expressed antibody to the antigen specifically recognised by K121. The wells of the second assay plate were coated with human free kappa light chains (50 μl/well of 100 μg/ml solution). In the second ELISA, clarified CHO cell supernatant showed binding to human free kappa light chains over a range of sample dilutions (FIG. 11b). By comparison no binding was observed for untransfected CHO cell conditioned medium.

EXAMPLE 11

Purification of cK121

Purification of cK121 was carried out by ammonium sulphate precipitation of proteins in the conditioned CHO cell medium (1.4 liter). After extensive dialysis of the resolubilized protein in PBS-Az the sample was subjected to affinity purification on Protein A agarose (Sigma Aldrich, USA). Eluted samples were dialysed in PBS pH 7.4, concentrated on an Amicon stirred cell (Millipore, USA) and filter sterilized (Minisart RC15, 0.2 μm, Sartorius, AG). The concentration of cK121 was estimated using an extinction coefficient of 14 at an absorbance of 280 nm.

EXAMPLE 12

Cytotoxicity of cK121 on HMy2 and K562 Lymphoblastoid Cells

Figure 12:
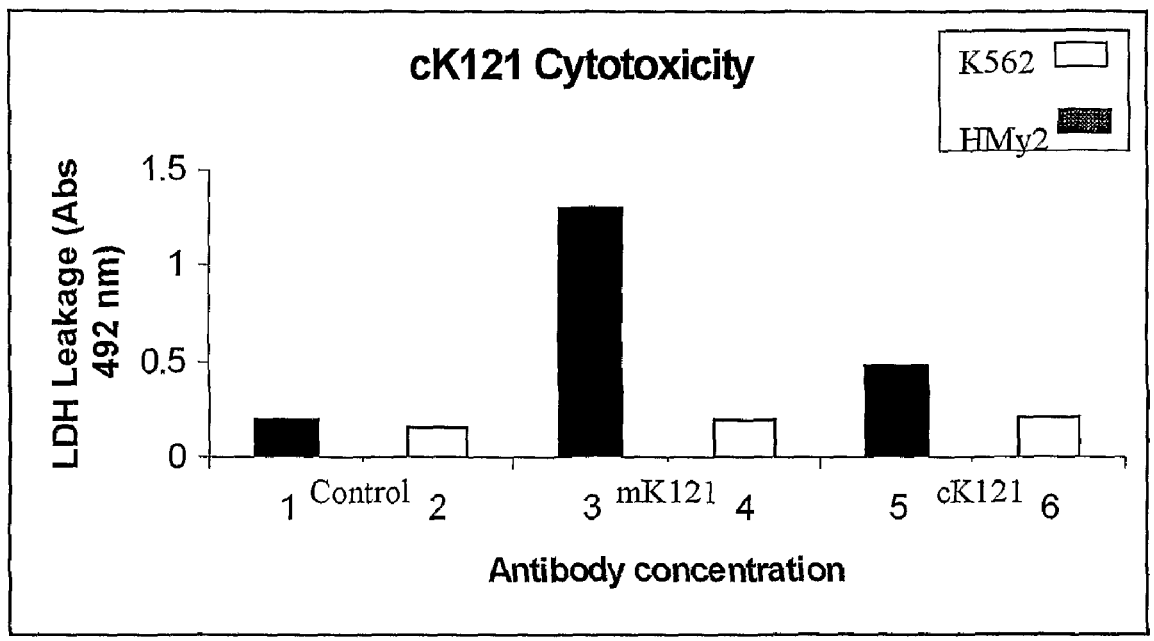
FIG. 12. Cytotoxic activity of chimaeric K121 (cK121) on HMy2 and K562 lymphoblastoid cells as measured by the leakage of cytoplasmic LDH Target cells were incubated in the presence of PBS (control), 5.5 µM murine K121 (mK121) or 0.8 µM chimaeric K121 (cK121) for 20 h at 37° C. in an atmosphere of 5% CO2.

Cytotoxicity of cK121 on HMy2 and K562 lymphoblastoid cells was determined using the leakage of cytoplasmic LDH assay as described in Example 1. The purified cK121 exhibited significant cytotoxic activity against antigen-positive HMy2 cells and did not react with the non-antigen bearing cell line, K562 (FIG. 12). These results indicate that cK121 has retained the ability to induce cell death in the target cell line. To confirm that the mechanism of cell death is apoptosis the assays described in example 2 should be performed on HMy2 cells using purified cK121.

EXAMPLE 13

Selection of Stable cK121 Secreting Cells

Figure 13:
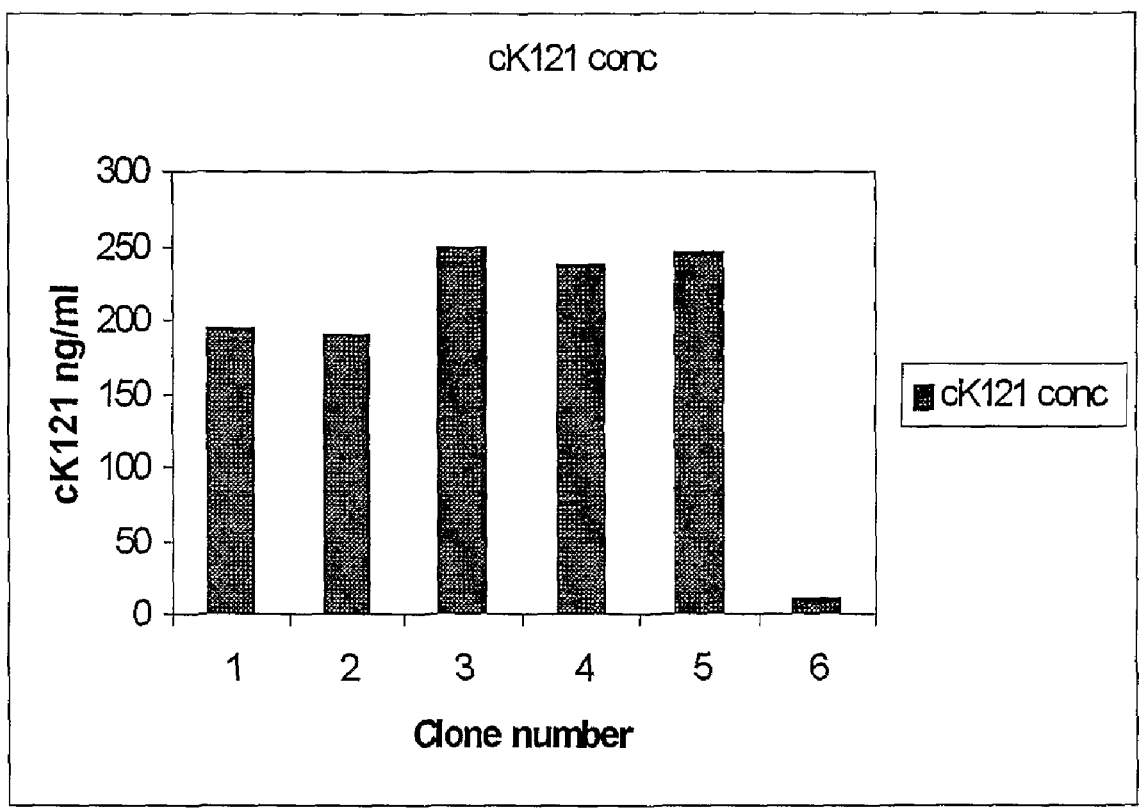
FIG. 13. Concentration of cK121 secreted by individual clones The concentration of cK121 was determined by an ELISA using anti-human IgG, IgA and IgM coated wells. Data represents positive clones 1-5 and a negative clone 6.

Large-scale production of cK121 requires selection of a cell line that is capable of stable antibody secretion in the absence of selection antibiotic, G418. Therefore, clones from the wells that produced positive results in both ELISA's (A 405 nm>0.2) were selected and cloned by limiting dilution. Subsequently, CHO cells from single clones that were capable of producing secreted cK121 were grown in DMEM-F12 without the antibiotic. Cells that continued to secrete cK121 in the absence of antibiotic were selected as stable cK121 producing cell lines. Conditioned medium from cK121 CHO cell lines was assessed by immunoassay as described in Example 9 and the amount of antibody produced was determined from the human IgG1 kappa standard curve. FIG. 13 shows 5 positive clones that were selected for future expression (clones 1-5). A negative clone was included as a control sample.

In order to carry out further functional studies on the cK121 clones produced in Example 13 a large-scale expression experiment may be conducted. The cK121 may be purified and in vivo animal study experiments may be performed.

EXAMPLE 14

Figure 14A:
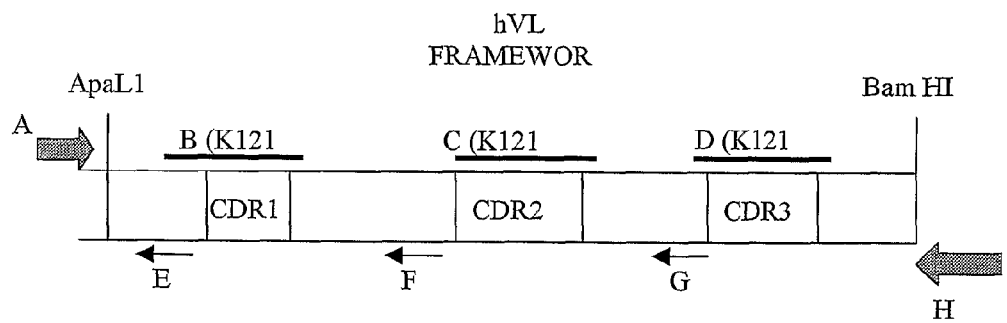
FIG. 14 (a) Schematic representation of a method for humanisation of K121 VL using a human VL gene as a framework. (b) The DNA sequence of a human framework VL and K121 VL. (c) Oligonucleotides for K121 VL humanisation using PCR.
Figure 14A:
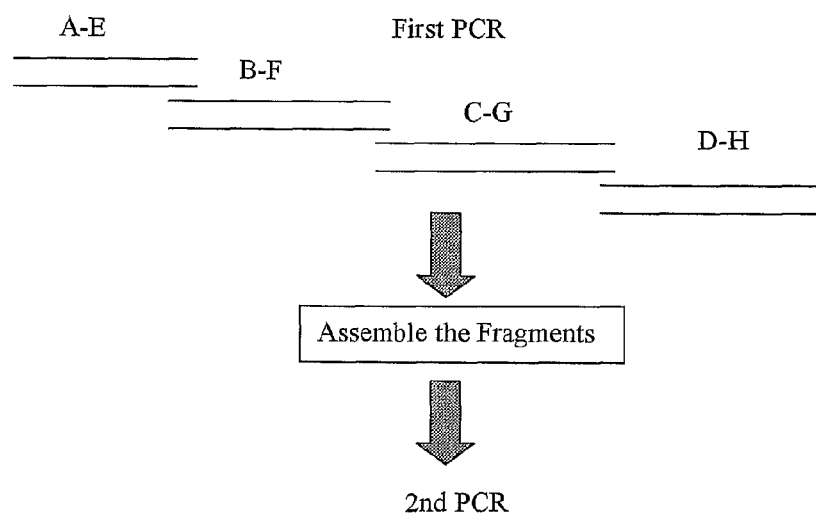

Strategy to Humanise the K121 Variable Light Chain Region Gene (VL) Using a Vκ Human VL Framework Region A schematic outline of the PCR procedure used to humanise K121 VL is depicted in FIG. 14a. The human VL framework region (hVL) was previously identified and isolated from cDNA using a PCR based strategy previously described (Asvadi, PhD Thesis, UTS, 1998). Plasmid DNA from a single clone containing the hVL gene was sequenced and is compared with the DNA sequence of K121 VL in FIG. 14b. DNA sequence shown in bold encodes the complementarity determining regions (CDR's) of K121. The oligonucleotides used to incorporate the DNA sequence for CDR1, CDR2 and CDR3 of K121 into the framework region of hVL are shown in FIG. 14c. The framework region containing the K121 CDR2 can be distinguished from hVL by digestion of the genes with the restriction enzyme Age1 and the restriction site is shown in the PCR primer VLC.

PCR Amplification

As shown in FIG. 14a the template for PCR amplification was the hVL gene and the reactions in the first PCR were carried out using primer pairs VLA+VLE, VLB+VLF, VLC+VLG and VLD+VLH. Amplification of the four fragments was carried out using the TITANIUM Taq PCR kit (Clontech, Calif.). The products from each reaction were visualised by agarose gel electrophoresis with ethidium bromide and isolated by gel extraction (Promega, Mass.). A second PCR was carried out to assemble the four amplified fragments. The resulting amplified product was approximately 380 bp. The DNA band was gel extracted and ligated into the vector pGEM-T according to the protocol recommended by the manufacturer (Promega, Mass.). An aliquot of the ligation mixture was transformed into JM109 heat competent cells and samples were plated out on LB-amp plates. Following overnight incubation at 37° C., single colonies were picked and grown overnight in SOC medium according to the protocol (Promega, Mass.). Plasmid DNA was isolated using a Wizard Plus Miniprep DNA purification system. Ten clones were subjected to digestion with the restriction enzymes Age1 and Bam H1 according to the recommended digestion procedure (Promega, Mass.). Products from the digestion were visualised on a 1% agarose gel containing ethidium bromide. A single clone that produced a DNA fragment of approximately the correct size should be sequenced to confirm that the insert contains the modified VL gene. The humanised K121 VL gene should then be ligated into the mammalian expression vector pCMV-KR as described in Example 9.

EXAMPLE 15

Humanisation of the K121 Variable Region Gene of the Heavy Chain (VH) Using a Human VH3 Framework Gene The human heavy chain variable region gene, hVH, was isolated and cloned using a PCR strategy as described in Example 14. A pGEM-T plasmid containing the hVH gene was used as template for the QuikChange Site-Directed Mutagenesis Kit procedure (FIG. 15a). Primers used to incorporate the three CDR's from K121 VH into the hVH framework are depicted in FIG. 15b. After each round of mutagenesis the plasmid should be sequenced to confirm that the DNA sequence is correct. The humanised K121 VH gene should then be ligated into the mammalian expression vector pCMV-γ1 as described in Example 9.

DISCUSSION

The experiments detailed herein demonstrate that the murine monoclonal antibody K121 induces cell death in a human lymphoblastoid cell line, HMy2, in the absence of any accessory effector cells or added serum complement proteins. We have previously shown that HMy2 cells express an antigen, KMA, which is recognized by K121. When HMy2 cells were incubated with K121 alone at a concentration of 3.6 μM, significant cell death occurred as indicated by the release of intracellular LDH (FIG. 1).

The specificity of the cytotoxic activity of K121 is demonstrated by the fact that treatment of a KMA negative cell line, K562, did not result in significant cell death (FIG. 1).

Microscopic observation of HMy2 cells incubated in the presence or absence of K121 indicated that cell death occurred in the presence of K121. In the presence of K121 cells appeared to shrink and there was evidence of membrane "blebbing". These effects are typical of cells undergoing a process termed programmed cell death or apoptosis (Kerr, J F R. et al., (1972) Br J Cancer 26:239). By contrast, incubation of HMy2 cells with the immunotoxin scFv-mel resulted in cell clumping and membrane lysis. Clearly, the appearance of cells incubated with K121 was different to those incubated with the immunotoxin, scFv-mel. These preliminary observations suggest that the mechanism resulting in cell death using K121 is different to the cytotoxic effect of scFv-mel.

Figure 2:
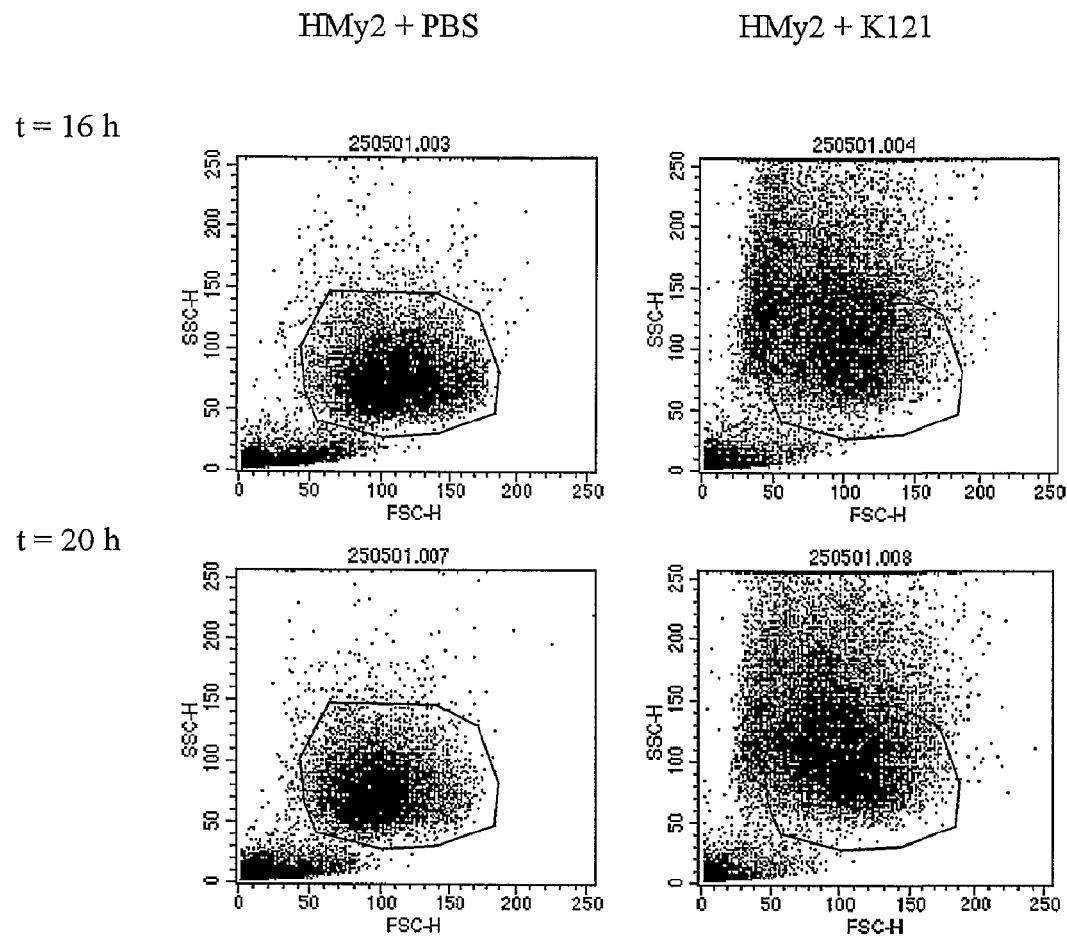
FIG. 2. Flow cytometric analysis of K121-induced apoptosis of HMy2 cells. Light scatter profile of HMy2 cells incubated with PBS or K121 for 16 and 20 h. FSC and SSC correspond to cell size and cell complexity respectively.
Figure 5:
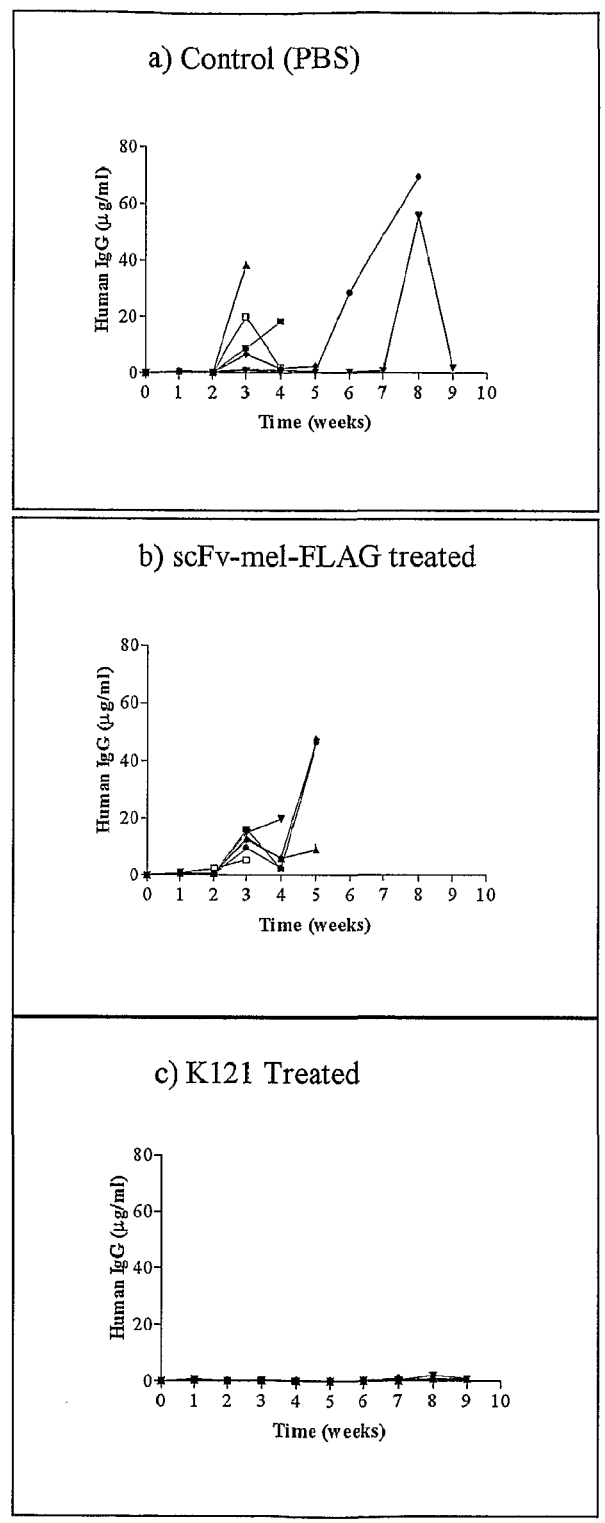
FIG. 5. Time course of serum levels of human IgG secreted by Hmy2 in SCID mice after (a) no treatment (PBS), (b) treatment with scFv-mel or (c) treatment with K121 mAb. Cells ($10^7$) were injected i.p. on day 0 and treatment with scFv-mel (0.5 mg/dose) or K121 mAb (1.25 mg/dose) given on days 1-3. Within a treatment group, each symbol represents IgG values for an individual mouse.

Analysis of the light scatter properties of HMy2 cells undergoing K121-induced cell death revealed changes in internal structure and size of the cells that were consistent with apoptosis (FIG. 2). This interpretation of the mechanism by which K121 kills target cells was confirmed by two separate assays for apoptosis that measure early and late stages of the process respectively (FIGS. 3 & 4). Thus, K121, in the absence of any exogenous factors, induces apoptosis in KMA-bearing cells in vitro. Furthermore, K121 prevents the growth of tumour cells in vivo, Administration of K121 to mice that had received a tumour-inducing dose of HMy2 cells prevented tumour growth as measured by the presence of human IgG in the serum of recipient mice (FIG. 5). Tumour growth was observed in all mice in the PBS treated group as indicated by levels of serum human IgG and gross morphology upon dissection.

Apoptosis is an important biological event involved in embryonic development and, in particular, the development and functioning of the immune system (Mastrangelo A J. and Betenbaugh M. (1998) TIBTECH. 16:88). In contrast to cell death arising from necrosis, apoptosis occurs in the absence of any pathology and does not evoke an inflammatory response (Kerr, J F R. et al., (1972) Br J Cancer 26:239). This is an important consideration with regard to the use of potential therapeutic agents that may trigger apoptosis in target cells.

All publications referred to above are incorporated herein in their entirety by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method for autologous hematopoietic cell transplantation in a subject, the method comprising:
    transplanting a hematopoietic progenitor cell population into the subject,
    wherein the hematopoietic progenitor cell population has been obtained from the subject and has been treated with an antibody,
    wherein the antibody is not conjugated to a toxin or a cytolytic agent, and wherein the antibody comprises a VH region set forth in SEQ ID NO:1 and a VL region set forth in SEQ ID NO:3 or binds the same epitope of kappa myeloma antigen (KMA) as an antibody comprising a VH region set forth in SEQ ID NO:1 and a VL region set forth in SEQ ID NO:3, wherein the antibody is effective to kill KMA-bearing myeloma cells.

2. The method of claim 1 wherein, the method further comprises intravenous infusion of an antibody into the subject.

3. The method of claim 1 wherein the method of autologous transplantation is performed on the subject during or after cytoreductive therapy.

4. The method of claim 1, wherein the antibody is a monoclonal antibody.

5. The method of claim 1, wherein the antibody binds the same epitope of kappa myeloma antigen (KMA) as an antibody comprising a VH region set forth in SEQ ID NO:1 and a VL region set forth in SEQ ID NO:3 and comprises the CDR loops (CDR1, CDR2 and CDR 3) of the K121 antibody as shown in FIG. 9a.

6. The method of claim 1 wherein the antibody is a chimaeric antibody or a humanised antibody.

7. The method of claim 1, wherein the method comprises administering chemotherapy to the subject.

8. The method of claim 1, wherein the method comprises administering radiotherapy to the subject.

9. The method of claim 1, wherein the cell population comprises KMA bearing, kappa-type myeloma cells.

10. The method of claim 5, wherein the antibody is a monoclonal antibody.

11. The method of claim 5, wherein the antibody is a chimaeric antibody or a humanised antibody.

* * * * *